United States Patent [19]
Smith et al.

[11] Patent Number: 5,431,645
[45] Date of Patent: Jul. 11, 1995

[54] REMOTELY ACTIVATED ENDOSCOPIC TOOLS SUCH AS ENDOSCOPIC BIOPSY FORCEPS

[75] Inventors: Kevin W. Smith, Coral Gables; Matthew A. Palmer, Miami; Sergio Rodriguez, Miami; John R. Whittier, Miami; Anthony Mazzeo, Fort Lauderdale, all of Fla.

[73] Assignee: Symbiosis Corporation, Miami, Fla.

[21] Appl. No.: 62,891

[22] Filed: May 17, 1993

Related U.S. Application Data

[63] Continuation-in-part of Ser. No. 16,595, Feb. 11, 1993, abandoned, and a continuation-in-part of Ser. No. 42,606, Apr. 2, 1993, and a continuation-in-part of Ser. No. 865,913, Apr. 9, 1992, Pat. No. 5,228,451, and a continuation-in-part of Ser. No. 837,046, Feb. 18, 1992, which is a continuation of Ser. No. 521,766, May 10, 1990, Pat. No. 5,133,727.

[51] Int. Cl.[6] .............................. A61B 17/00
[52] U.S. Cl. ......................... 606/1; 606/46; 600/106; 600/117; 600/126
[58] Field of Search .................. 128/4, 6, 751, 752; 606/1, 46–47, 205, 206, 207

[56] References Cited

U.S. PATENT DOCUMENTS

| | | | |
|---|---|---|---|
| 3,266,494 | 8/1966 | Brownrigg et al. | 606/206 |
| 4,757,814 | 7/1988 | Wang et al. | |
| 5,094,247 | 3/1992 | Hernandez et al. | |
| 5,179,935 | 1/1993 | Miyagi | 128/4 |
| 5,197,963 | 3/1993 | Parins | 606/46 |
| 5,259,365 | 11/1993 | Nishikori et al. | 128/4 |
| 5,269,289 | 12/1993 | Takehana et al. | 128/4 |

Primary Examiner—Stephen C. Pellegrino
Assistant Examiner—Michael Peffley
Attorney, Agent, or Firm—David P. Gordon

[57] ABSTRACT

Remote control actuators for endoscopic tools are provided. Each remote control actuator includes a driver, a coupler which couple the endoscopic tool to the driver, a power source which power the driver, and a controller coupled to the power source and/or the driver for controlling the power applied to the driver. In conjunction with the controller, a user interface is preferably provided for user control of the remote control actuator which actuates the endoscopic tool. In addition, a sensing/feedback mechanism is preferably provided between the driver and the endoscopic tool and is coupled to the controller and/or the power source. The sensing/feedback mechanism senses the amount of tension or compression on the pull wire(s) of the endoscopic tool and provides a related signal to the controller so that the force applied to the endoscopic tool may be regulated. Various types of power sources are disclosed including electric, mechanical, hydraulic, and pneumatic. Various types of drivers are disclosed, including a motor/linear actuator, a hydraulic or pneumatic piston, and a motor with or without reduction gears coupled to a pulley and belt or a sprocket and chain or a rack and pinion. In addition, several couplers, controllers, user interfaces, and sensing/feedback mechanisms are disclosed.

44 Claims, 24 Drawing Sheets

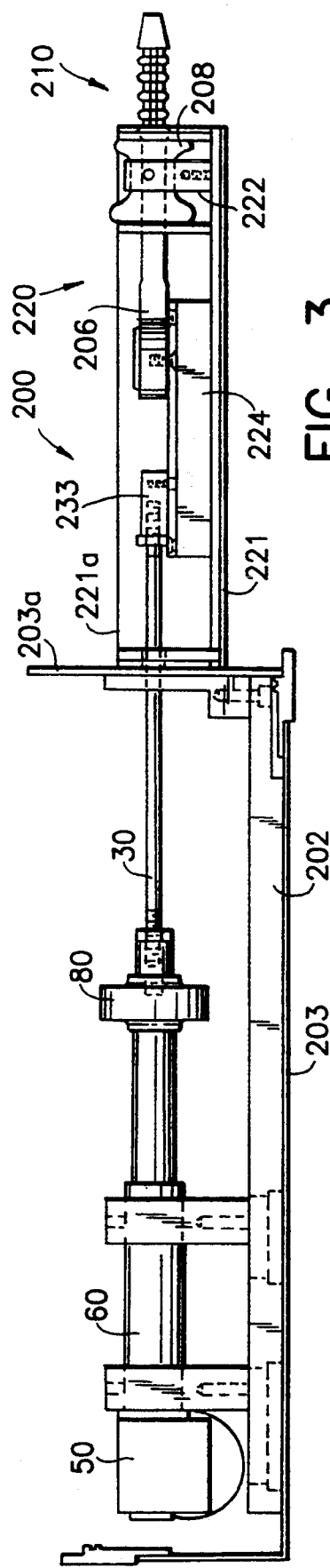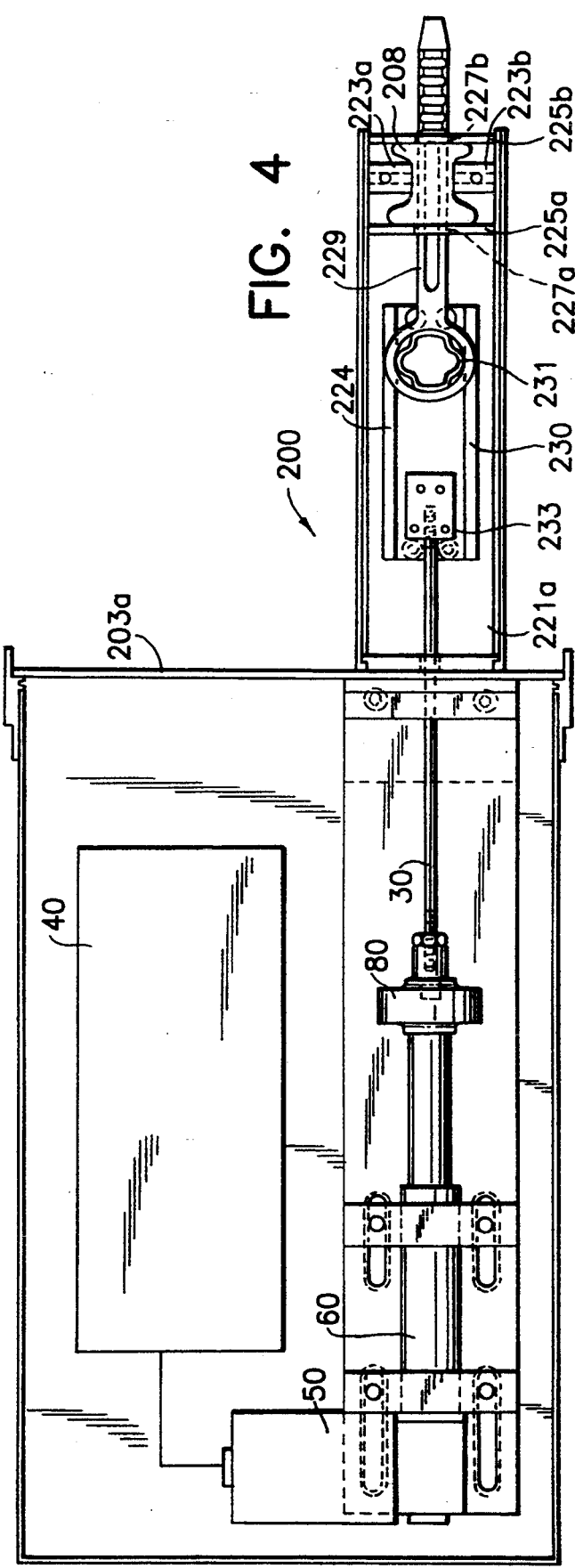

SERVO SYSTEM

REMOTELY ACTIVATED ENDOSCOPIC TOOLS SUCH AS ENDOSCOPIC BIOPSY FORCEPS

This application is a continuation-in-part of application U.S. Ser. Nos. 08/016,595 (now abandoned) (Endoscopic Biopsy Forceps Devices with Selective Bipolar Cautery) filed Feb. 11, 1993, 08/042,606 (Biopsy Forceps Having Detachable Proximal Handle and Distal Jaws) filed Apr. 2, 1993, 07/865,913 (Biopsy Forceps Device Having Stiff Distal End) filed Apr. 9, 1992, now issued as U.S. Pat. No. 5,228,451 and 07/837,046 (Radial Jaw Biopsy Forceps) filed Feb. 18, 1992 which is a continuation of U.S. Ser. No. 07/521,766 now issued as U.S. Pat. No. 5,133,727, all of which are hereby incorporated by reference herein in their entireties.

BACKGROUND OF THE INVENTION

1. Field of the Invention

The invention relates to surgical instruments. More particularly, the invention relates to an apparatus for the automatic remote control of endoscopic surgical instruments such as endoscopic biopsy forceps devices.

2. State of the Art

Endoscopic surgery is widely practiced throughout the world today and its acceptance is growing rapidly. In general, endoscopic surgery involves the use of a camera or optical system inserted through a tube, while a cutter, dissector, or other surgical instrument is inserted through another tube for purposes of manipulating and/or cutting an internal organ or tissue under view of the surgeon via the camera or optical system. In endoscopic biopsy procedures, typically, the camera or optical system is located in one lumen of a flexible endoscope while a biopsy cutter is placed through another lumen thereof.

By 1996, it is expected that more than two million additional endosurgeries will be performed per year that, in 1990, were done via open surgery (MedPRO Month, I:12, p. 178). The advantages of endoscopic surgery are clear in that it is less invasive, less traumatic, and recovery is typically quicker. As a result, many new instruments and devices for use in endosurgery are introduced every year. Most endoscopic instruments have similar configurations with a proximal handle, an actuation mechanism, and distal end effectors coupled by a tube through which the actuation mechanism extends. (As used herein, "proximal" means closest to the surgeon and farthest from the surgical site, while "distal" means farthest from the surgeon and closest to the surgical site.) The end effectors take many forms such as grippers, cutters, forceps, dissectors and the like.

Endoscopic instruments in use today may be broadly classified as two types: reusable; and disposable. Parent application Ser. No. 08/042,606 and the parent thereof, Ser. No. 08/016,596 relate to a third type of endoscopic instrument which is separable into a reusable portion and a disposable portion.

A number of different types of biopsy forceps are in common use, typically in conjunction with endoscopic assistance. These devices most often include sharp opposing jaws for grasping and tearing tissue for biopsy. The jaws are mated with one another about a clevis pin which is mounted in a clevis. The clevis extends into a housing which is crimped to the distal end of a relatively long flexible coil. The proximal end of the coil is coupled to a handle having means for articulating the jaws. The handle generally includes a central slotted shaft about which a spool is disposed. One or more pull wires from the jaws extend through the coil and are attached to the spool while the coil is attached to the central shaft of the handle. Movement of the spool relative to the central shaft moves the pull wires relative to the coil and thus articulates the jaws at the distal end of the coil. The handle is usually provided with a thumb ring at its proximal end. Movement of the spool relative to the handle is effected by inserting a thumb through the thumb ring, surrounding the spool with two fingers, and moving the thumb relative to the fingers in an action similar to operation of a hypodermic syringe. Although it is possible to operate the forceps in other ways, accurate operation generally requires the use of three digits.

When using the forceps, the jaws and coil are inserted through a flexible endoscope which is already in place in the patient's body. The surgeon holds the endoscope while viewing the biopsy site through the optical system and guides the coil and jaws to the biopsy site while a nurse holds the handle. When the surgeon has located the jaws at the appropriate place, the nurse is instructed verbally to operate the handle to articulate the jaws and grasp a biopsy sample. Because both of the surgeon's hands are occupied holding the endoscope and the coil of the forceps, the surgeon cannot operate the forceps directly. As a result, a biopsy procedure utilizing an endoscopic biopsy forceps requires the time and presence of, and room for two skilled practitioners instead of one.

SUMMARY OF THE INVENTION

It is therefore an object of the invention to provide means for actuating an endoscopic tool, in particular a biopsy forceps, which can be operated by a surgeon while both hands are occupied by an endoscope and/or other devices.

It is also an object of the invention to provide a remote control actuation means for actuating an endoscopic tool such as a biopsy forceps, where the surgeon can operate the actuation means with a single finger.

It is another object of the invention to provide remote control actuation means for actuating an endoscopic tool where the force applied to the end effectors of the endoscopic tool is accurately adjustable prior to actuation.

It is still another object of the invention to provide a remote control actuation means for actuating an endoscopic tool, in particular a biopsy forceps, where the surgeon can operate the actuation means by a foot pedal.

It is a further object of the invention to provide a remote control actuation means for actuating an endoscopic tool, in particular a biopsy forceps, where the surgeon can operate the actuation means by voice command.

It is still a further object of the invention to provide a remote control actuation means for actuating a biopsy forceps, which quickly and easily couples to a conventional endoscopic biopsy forceps device.

It is an additional object of the invention to provide a remote control actuation means for actuating an endoscopic tool, such as a biopsy forceps, which quickly and easily couples to a disposable distal portion of the endoscopic tool.

Yet another object of the invention is to provide a remote control actuation means for actuating an endoscopic biopsy forceps where the actuation means dynamically applies a force to hold the end effectors of the biopsy forceps in a lightly closed position during insertion and withdrawal through an endoscope.

In accord with these objects which will be discussed in detail below, the remote control actuator of the present invention which actuates an endoscopic tool broadly includes a driving means, a coupling means for coupling the endoscopic tool to the driving means, a power source means for powering the driving means, and a controller means coupled to the power source means and/or the driving means for controlling the power applied to the driving means. In conjunction with the controller means, a user interface is preferably provided for user control of the remote control actuator which actuates the endoscopic tool. In addition, sensing/feedback means is preferably provided between the driving means and the endoscopic tool and is coupled to the controller means and/or the power source means. The sensing/feedback means senses the amount of tension or compression on the pull wire(s) of the endoscopic tool and provides a related signal to the controller means so that the force applied to the endoscopic tool may be regulated.

Various types of power sources are provided, including electric, mechanical, hydraulic, and pneumatic. Likewise, various types of driving means are provided, including: a motor/linear actuator, a hydraulic or pneumatic piston, and a motor with or without reduction gears coupled to a pulley and belt or a sprocket and chain or a rack and pinion.

Several means for coupling the endoscopic tool to the driving means are also described. One means for coupling the driving means to a conventional biopsy forceps includes separate means for holding the spool and the handle of such a conventional tool. Another means for coupling the endoscopic tool to the driving means comprises separate means for capturing the proximal ends of the coil and wire of the distal portion of a separable biopsy forceps such as those described with reference to the proximal reusable handle in parent application Ser. No. 08/042,606.

The controller means includes means responsive to the user interface so that the power supply means and/or the drive means may be regulated for opening and closing the end effectors of the endoscopic instrument. Preferably, the controller means can cause the drive means to effect in the end effectors of the endoscopic instrument the obtaining and maintaining of open and closed positions, the obtaining and maintaining of an idle low force closed position (e.g., during insertion and withdrawal through the scope), and the bringing of the drive means to a predetermined coupling position for coupling and uncoupling the endoscopic instrument to and from the coupling means. The implementation of the means for controlling the driving means depends, among other things, on whether the driving means is "self-locking" or "non-locking", i.e. whether or not the driving means changes its position in response to an externally applied force when power is removed.

A variety of user interfaces are provided, including a finger activated pushbutton(s) or trigger-like switch attached to an endoscope, a foot switch, a voice recognition circuit, and a trigger-like switch. The user interface is coupled to the controller means by wire or through wireless means such as infrared or RF coupling. The user interface of the controller means is preferably provided with a user control which can direct the amount of movement of the driving means and thus the closing force applied to the end effectors of the endoscopic instrument. If desired, the user interface can also be provided with a rate control which can direct the rate at which the driving means operates.

Several sensing/feedback means are disclosed, including: a load cell which senses the force applied by the driving means; a single spring/switch combination which senses a threshold force applied to the driving means; a multiple spring/switch combination which indicates various force conditions; a position sensor which senses the amount of movement of the driving means and/or in cooperation with a spring senses the force applied by the driving means. Yet other sensing/feedback means include: an LVDT (linear variable displacement transformer) or other position sensing device such as an encoder, with or without a spring; a current sensing means which is used in conjunction with an electric driving means of non-locking variety; and a pressure transducer which is used in conjunction with either pneumatic or hydraulic driving means. The sensing/feedback means is used in conjunction with the controller means to vary the power supplied by the power source to the driving means such as by varying the current/voltage to an electric driving means, or by varying the pressure to a pneumatic or hydraulic driving means.

Additional objects and advantages of the invention will become apparent to those skilled in the art upon reference to the detailed description taken in conjunction with the provided figures.

BRIEF DESCRIPTION OF THE DRAWINGS

FIG. 3 is a side elevational view of one embodiment of the remote control apparatus of the invention having coupling means for coupling the invention to a conventional biopsy forceps;

FIG. 4 is a top plan view of the embodiment of FIG. 3;

FIG. 20b is a top plan view of the embodiment of FIG. 20a; and

FIG. 20c is a schematic side view of the proximal portion of the embodiment of FIG. 20a.

DETAILED DESCRIPTION OF THE PREFERRED EMBODIMENTS

1. Broad Description of Structure of the Invention

Figure 1:
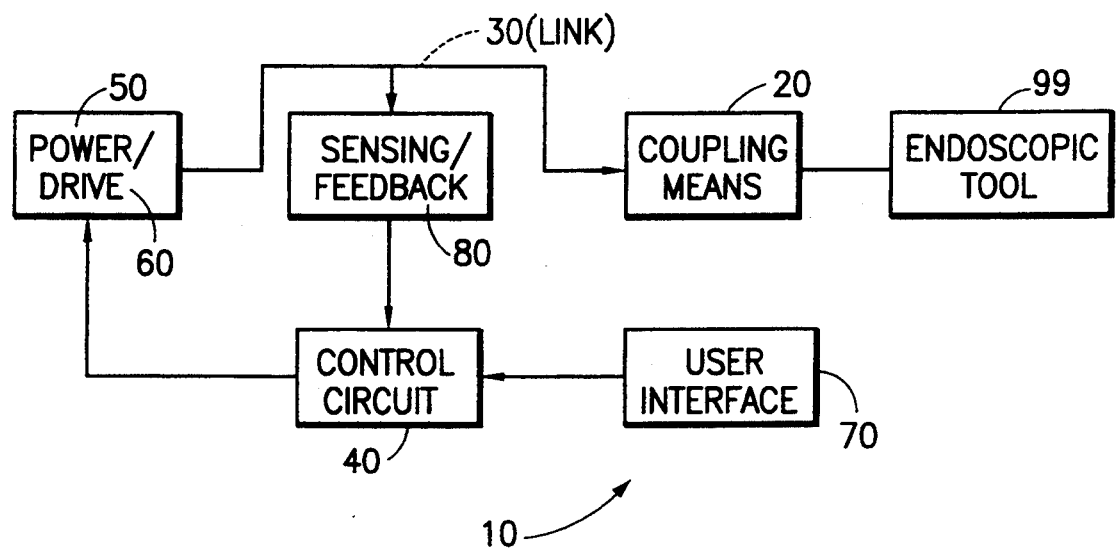
FIG. 1 is a schematic block diagram of the automatic remote control apparatus of the invention for controlling an endoscopic instrument.

Referring now to FIG. 1, the remote control actuator 10 of the invention broadly comprises a driving means 60, a coupling means 20 for coupling the endoscopic tool to the driving means 60, a power source means 50 for powering the driving means 60, and a controller means 40 coupled to the power source means 50 and/or the driving means 60 for controlling the power applied by the driving means 60 to the coupling means 20. In conjunction with the controller means, a user interface 70 is preferably provided for user control of the remote control actuator which actuates the endoscopic tool. In addition, sensing/feedback means 80 is preferably provided between the driving means 60 and the endoscopic tool 99 and is coupled to the controller means 40 and/or the power source means 50. The sensing/feedback means senses the amount of force exerted on the endoscopic tool and provides a related signal to the controller means 40 so that the force applied to the endoscopic tool may be regulated. If desired, a link 30 may be provided between the drive means 60 and the coupling means 20.

Those skilled in the art will appreciate that most endoscopic tools are provided with an actuating proximal end having two parts movable relative to each other. Thus, the function of the coupling device 20 is to allow these parts to be moved relative to each other, typically by holding one of the parts stationary while allowing the other of the parts to be moved by the actuator 10. For purposes of convenience, as well as for purposes of describing the preferred embodiment, the invention will hereafter be described with reference to an endoscopic biopsy forceps device as opposed to a scissor-type handled device such as a laparoscopic device. It will be appreciated, however, that the concepts disclosed herein apply to both types of devices, as well as to other endoscopic devices.

As will be described in greater detail below, the coupling device 20 may be arranged to couple the invention to a conventional biopsy forceps or to the distal disposable portion of the separable biopsy forceps described in parent application Ser. No. 08/042,606. The coupling device 20 may be directly connected to the drive means 60, or may be coupled via a link 30 as described above.

The power source 50 may be electric, mechanical, pneumatic or hydraulic as will be described below. The power source 50 is coupled to a controller means 40 which in turn is coupled to and is responsive to a user interface 70. The user interface may be finger operated, foot operated, voice operated, or operated by a combination thereof as will be described in detail below.

A sensing/feedback device 80 is preferably interposed between drive means 60 and coupling device 20. When so interposed, the linkage 30 may comprise a first and second linkage between which parts the sensing-/feedback device 80 is located. The sensing/feedback device 80 may be a position sensor, a force sensor (e.g., a load cell or a pressure transducer), or a combination of both. The controller means 40 is coupled to the sensing-/feedback device 80 to receive signals regarding the position and/or force of the driving means 60 relative to the coupling device 20.

The controller means 40 may include circuits in the case of an electric power source or valves in the case of an hydraulic or pneumatic power source. In either case, the controller means 40 is responsive to certain commands entered from the user interface 70, and also to input received from the sensing/feedback device 80.

2. Broad Description of How the Remote Control Actuator Functions

Figure 2:
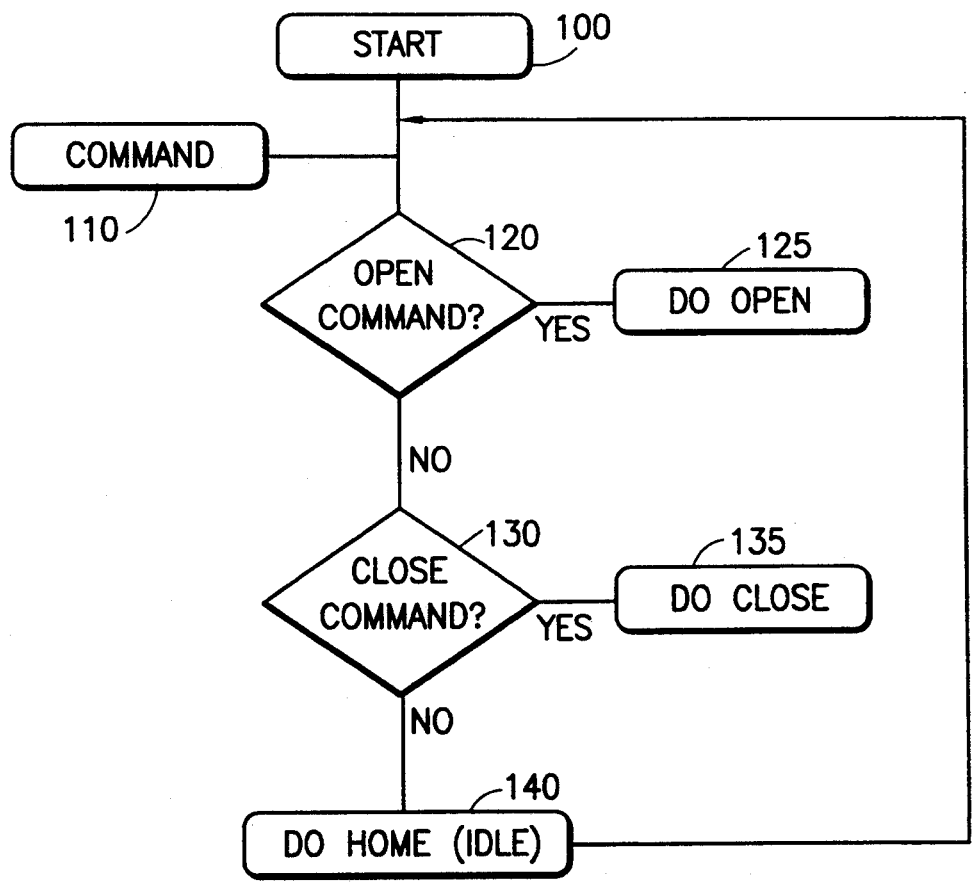
FIG. 2 is a flow chart of the operation of the apparatus of the invention.

The functioning of the remote control actuator is seen with reference to the flow chart of FIG. 2. Upon powering up of the remote control actuator at 100, the actuator looks at 110 for commands from the user interface such as an "open end effectors" command or a "close end effectors" command. Upon receiving a command at 110, the controller determines at 120 and 130 whether the command is to open or close the end effectors, and the actuator performs the required functions at 125, 135 to cause the power source to move the drive means so as to open or close the jaws of the forceps. In some embodiments of the invention, when no command is being issued by the user interface, the controller at 140 brings the jaws of the forceps into a "home" or "idle" (default) position which is preferably closed with a slight force between the jaws. In other embodiments of the invention, the controller effectively locks the jaws in the open or closed position until another command such as "home" is issued.

The default position is useful for permitting the endoscopic biopsy forceps device 99 to be inserted through an endoscope to the surgery site, as the device in the default position is under only slight tension and is easily manipulated through the endoscope. The default position is also useful in withdrawing the forceps out of the endoscope after a biopsy has been obtained as damage to the endoscope is limited while the biopsy sample is safely maintained in the jaws. As will be discussed in more detail below, in the idle (default) position, the apparatus of the invention dynamically senses the force on the pull wire(s) of the endoscopic instrument and constantly makes corrections in order to maintain the idle position force. This is important because when a biopsy forceps device is twisted through an endoscope, the position of the proximal end of the pull wire changes relative to the position of the proximal end of the outer tube or coil. This change in position is due to the differences in the radii of curvature of the coil and actuating wire within the coil. If the apparatus did not constantly adjust to maintain the idle force, then depending upon the state of the biopsy forceps device when it was connected to the apparatus of the invention, the jaws of the forceps could open as the biopsy forceps device was being fed through the endoscope, or the jaws of the forceps could open after the biopsy was taken as the biopsy forceps device is being removed. As will be appreciated by those skilled in the art, both situations would lead to unacceptable results.

3. Coupling Devices

3A. For Conventional Endoscopic Biopsy Forcep Devices

Turning now to FIGS. 3 and 4, a first embodiment a remote control actuator 200 is shown having a coupling device 220 for coupling the actuator to a conventional biopsy forceps 210 having a spool 208 and a thumb ring 206. As seen in FIG. 3, the control electronics 40, power source 50, drive means 60, and coupling device 220 are mounted appropriately on a frame 202 within a housing 203. The coupling device 220 is mounted in a housing extension 221 attached to side wall 203a of housing 203. The coupling device 220 includes a stationary part 222 and a movable part 224. It will be appreciated that the stationary part 222 is fixedly mounted to the housing extension 221, while the movable part 224 is movably mounted in the housing extension 221 so that it is linearly movable relative to the stationary part 222. The movable part 224 is coupled by linkage 30 to sensing/feedback device 80 which in turn is coupled to the drive means 60.

In the embodiment of FIGS. 3 and 4, the spool 208 of a conventional biopsy forceps 210 is held stationary by stationary part 222 of the coupling device 220 while the thumb ring 206 of the forceps 210 is coupled to the movable part 224 of the coupling device for movement by the drive means 60 through linkage 30. As seen best in FIG. 4, the stationary part 222 of the coupling device 220 includes two upstanding members 223a, 223b which cradle the narrow midsection of spool 208 and/or two upstanding members 225a, 225b having central openings 227a, 227b, which abut the top and bottom flanges of the spool 208 while allowing free passage of the handle 229 of the forceps 210. The movable part 224 of the coupling device 220 includes a sliding base 230 and an upstanding boss 231 which enters the thumb ring 206 of the forceps handle 229. Attachment means 233 attach the movable part 224 to the linkage 30 as described above. It will be appreciated that when the movable part 224 is brought into the coupling/uncoupling position as described above, the handle, thumb ring, and spool of the conventional forceps 210 can simply be placed into the coupling device with a minimum of effort. The spool is placed or dropped into the cradle formed for it by the stationary part and the thumb ring is placed or dropped over the boss of the movable part. Those skilled in the art will recognize that in this embodiment, operation of the forceps is by movement of the thumb ring relative to the spool whereas in a manual operation without the invention, most often the spool is moved relative to the thumb ring. However, it will be appreciated that the same effect is obtained so long as one is moved relative to the other.

It will be appreciated that the housing extension 221 housing the coupling device 220 must be accessible to the user and that is why it is formed as an extension from the main housing 203. While main housing 203 can be completely enclosed, it is desirable that housing extension 221 have an open or easily removable top portion 221a. Sliding base 230 preferably includes a ball bearing track (not shown). Linkage 30 preferably includes a push rod having threaded end connections.

3B. For Separable Endoscopic Biopsy Forcep Devices

Turning now to FIGS. 5, 5a, 6 and 6a, a second embodiment of a remote control actuator 300 is shown having a coupling device 320 for coupling the invention to the distal disposable portion 310 of a separable biopsy forceps as disclosed in parent application Ser. No. 08/042,606. Here, the actuating (proximal) end of the endoscopic forceps device includes a pull wire coupling 312 and a coil coupling 314. The coupling device 320 of this embodiment includes a stationary part 322 for coupling with the coil coupling 314 and a movable part 324 for coupling with the pull wire coupling 312.

The coil coupling 314 includes a mating sleeve 314a with a radial groove 314b. The stationary part 322 of the coupling device 320 includes a tube 322a having a throughbore 322b for receiving the pull wire coupling 312, pull wire 312a, and coil coupling sleeve 314a. A latch 323 passes perpendicularly through the tube 322a for engaging the radial groove 314b of the coil coupling 314 as described in greater detail in parent application Ser. No. 08/042,606. Latch 323 preferably includes a release button 323a and a spring 323b urging the latch into a locking position. It will be appreciated that the coil coupling could also be any of the embodiments mentioned in the previously incorporated parent application Ser. No. 08/042,606.

Tube 322a is also provided with a slot 322c and the movable part 324 of the coupling device 320 includes a cross block 324a which passes through the slot 322c. It will be appreciated that the movable part 324 of this embodiment of the coupling device resembles and is substantially the same as the spool disclosed in parent application Ser. No. 08/042,606. The cross block 324a is provided with spring biased sliders 324b, 324c which engage groove 312a in the conical mating tip of pull wire coupling 312. It will be appreciated that the latching mechanism in the spool could also be any of the embodiments mentioned in the previously incorporated parent application Ser. No. 08/042,606.

The spool-like movable part 324 of the coupling device 320 is coupled to load cell 80 by a pair of threaded rods 325a, 325b which thread into the spool 324 and into a beam or bracket 325c which is mounted to the top of the load cell 80.

A coupling of the endoscopic forceps device 310 to the coupling device 320 is accomplished by moving the spool-like movable part 324 to a coupling position as directed by the above-described controller 40. The proximal end of the endoscopic biopsy forceps instrument is inserted into the bore 322b of tube 322a whereupon the conical tip of pull wire coupling means 312 engages sliders 324b, 324c in the cross block 324a and the groove 314b in the sleeve 314a engages the latch 323.

Uncoupling the endoscopic biopsy forceps device 310 from the coupling device 320 is accomplished by moving the spool-like movable part 324 to an uncoupling position (maximum distal position) as directed by the controller described above. This movement disengages the mating tip 312 from the sliders 324b, 324c by the action of release collar 324d against the tube shoulder 322d. Latch 323 is then moved against spring 323b by pressing button 323a and the sleeve 314a is pulled from tube 322a with the mating tip 312 following. Additional details of the uncoupling may be understood with reference to parent application Ser. No. 08/042,606. It will also be appreciated that a user interface control (see FIGS. 13a, 13e, and 18e) may be provided for automatically moving the linear actuator or other drive means to effect loading and/or unloading of the endoscopic instrument.

4. Power Sources and Drive

4A. Linear Actuator

FIGS. 3-6 described above with reference to coupling devices also show a first embodiment of power source and drive means. In the preferred embodiment, the power source 50 and drive means 60 comprise a linear actuator such as the "Ball Drive Actuator 85615" manufactured by Motion Systems Corporation of Shrewsbury, N.J. It will be appreciated that the preferred linear actuator is a "self-locking" drive means and remains in its last position until powered to a different position. The use of a self-locking drive means suggests that the controller provide an idle mode command which permits the endoscopic instrument to automatically return to a low force closed dynamic state when not holding the biopsy forceps device in an open or fully closed position. With a non-locking drive means, other mechanisms, such as a spring can return the drive means to an idle state.

The preferred linear actuator of the invention moves forward and backward (linearly) based on the voltage provided to it motor by the voltage supply means. Typically, motors of the linear actuators require DC voltages of −12 V to 12 V with a negative voltage causing movement in one direction and a positive voltage causing movement in the other direction, although some linear actuator motors operate on low AC voltage. The fact that low voltages are utilized is advantageous in that there is minimal risk of shock to the patient or to the practitioner.

4B. Rack and Pinion

Figure 7:
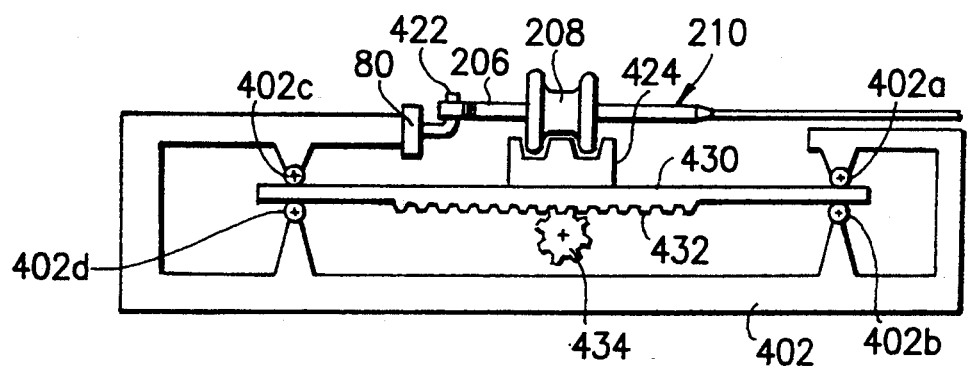
FIG. 7 is a side elevational view of another embodiment of the invention where the drive means includes a rack and pinion with an electric motor.
Figure 8:
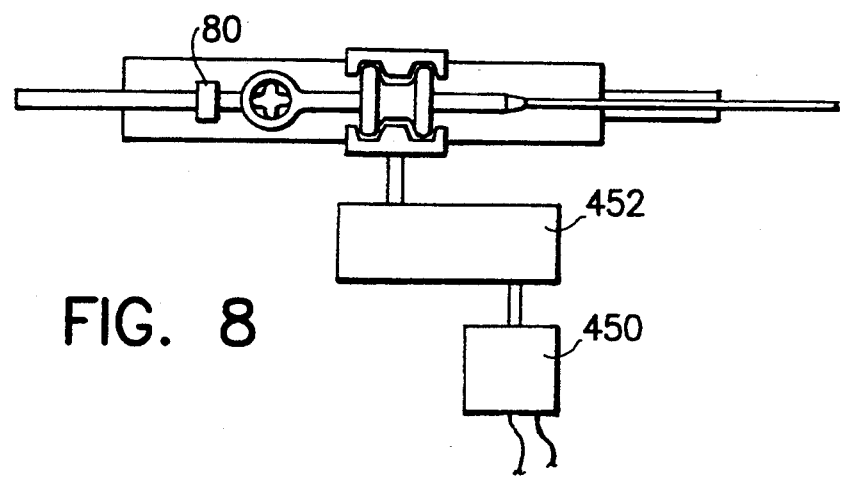
FIG. 8 is a top view of the embodiment of FIG. 7.

Turning to FIGS. 7 and 8, a rack and pinion drive means powered by an electric motor is shown. In this embodiment of the drive means, the stationary part 422 of the coupling device engages the thumb ring 206 of a conventional biopsy forceps device 210 and the movable part 424 engages the spool 208 of the device 210. The movable part 424 is directly coupled to a movable rack 430 carried on roller guides 402a–402d in frame 402. Rack 430 is provided with teeth 432 which are engaged by a pinion 434. Pinion 434 is coupled to a stepper motor 450 by means of a reduction drive 452.

In this embodiment, the sensing/feedback means 80 is located between the stationary part 422 (holding the thumb ring 206) and the frame 402. It will be appreciated, however, that the force applied on the spool 208 by the motor 450 through the moving part 424 results in an equal but opposite force on the thumb ring 206 which is measured by the sensing/feedback means 80.

The motor 450 may be either a stepper motor or a conventional motor, either AC or DC, preferably low voltage. Coupling the motor 450 to the pinion 434 may be direct or through a reducing drive as shown.

4C. Chain and Sprocket; or Belt and Pulley

Figure 9:
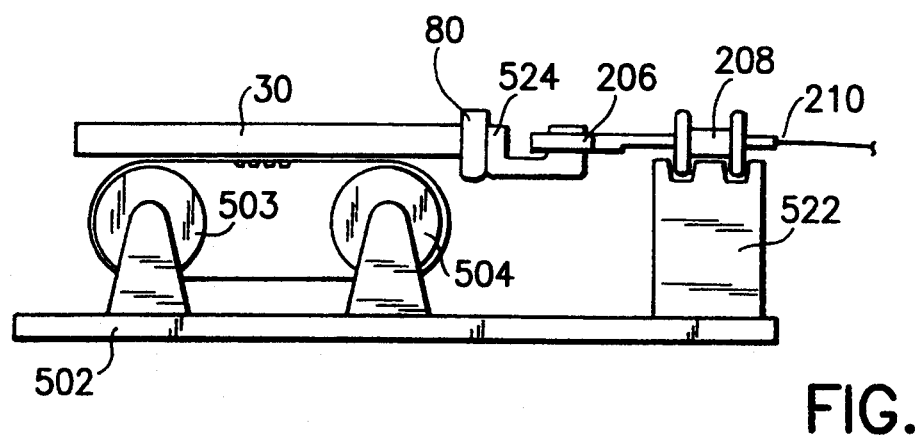
FIG. 9 is a side elevation view of another embodiment of the invention where the drive means is a belt/pulley or chain/sprocket with an electric motor.
Figure 10:
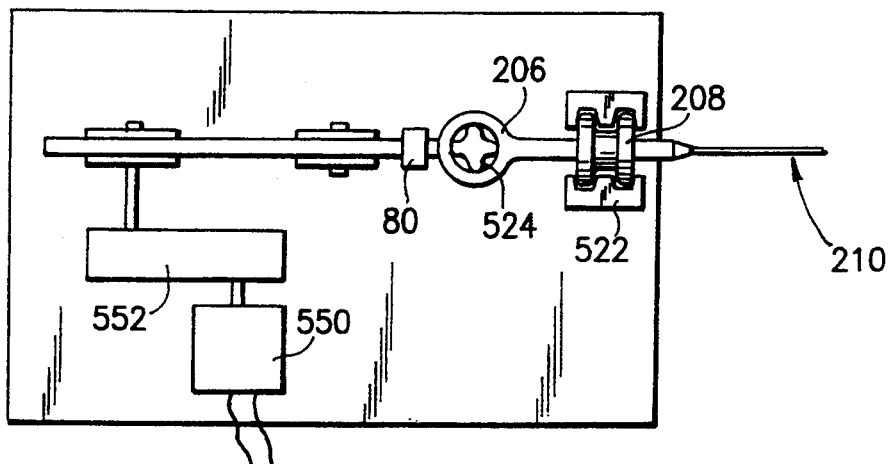
FIG. 10 is a top view of the embodiment of FIG. 9.

FIGS. 9 and 10 show the use of a chain or belt and sprocket or pulley drive means powered by an electric motor. In this embodiment, the stationary part 522 of the coupling device engages the spool 208 of a conventional endoscopic biopsy forceps device 210 and the movable part 524 engages the thumb ring 206. The movable part 524 is coupled to a load cell 80 which in turn is coupled to linkage 30. Linkage 30 is coupled to belt or chain 560 carried on pulleys or sprockets 503,504 attached to frame 502. An electric motor 550 is coupled to one of the pulleys, e.g. pulley 503, by an optional reduction drive 552.

4D. Hydraulic and Pneumatic

Figure 11:
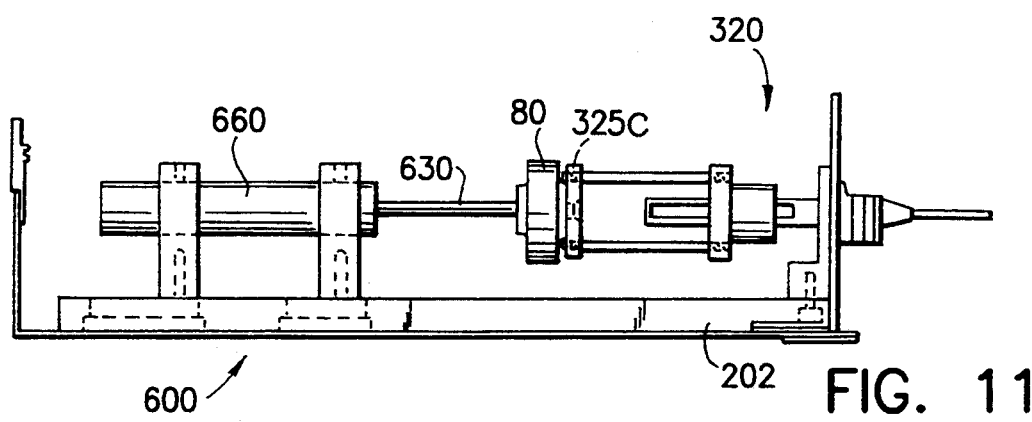
FIG. 11 is a side elevation view of another embodiment of the invention where the drive means is a pneumatic or hydraulic cylinder and the source means is a pressure or hydraulic fluid with flow metering valves.
Figure 12:
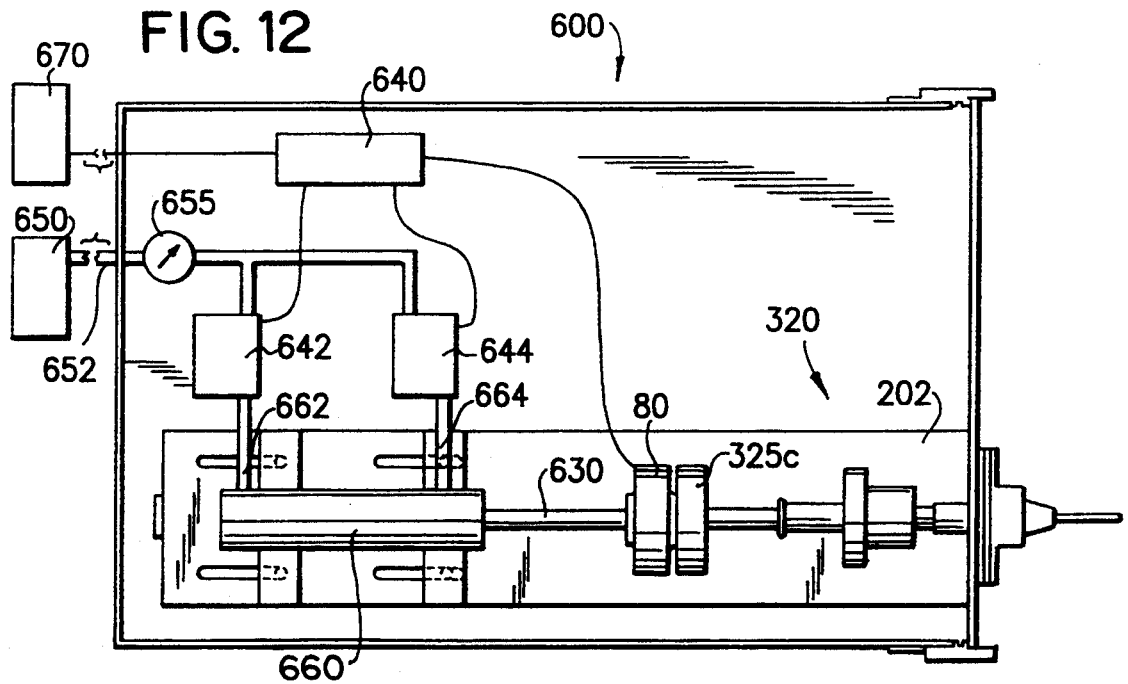
FIG. 12 is a top view of the embodiment of FIG. 11.

FIGS. 11 and 12 show the use of a pneumatic or hydraulic cylinder drive means powered by a source of pressurized air or hydraulic fluid. In the embodiment of FIGS. 11 and 12, the endoscopic biopsy forceps device is the distal disposable portion of a separable biopsy forceps as disclosed in parent application Ser. No. 08/042,606.

Figure 5:
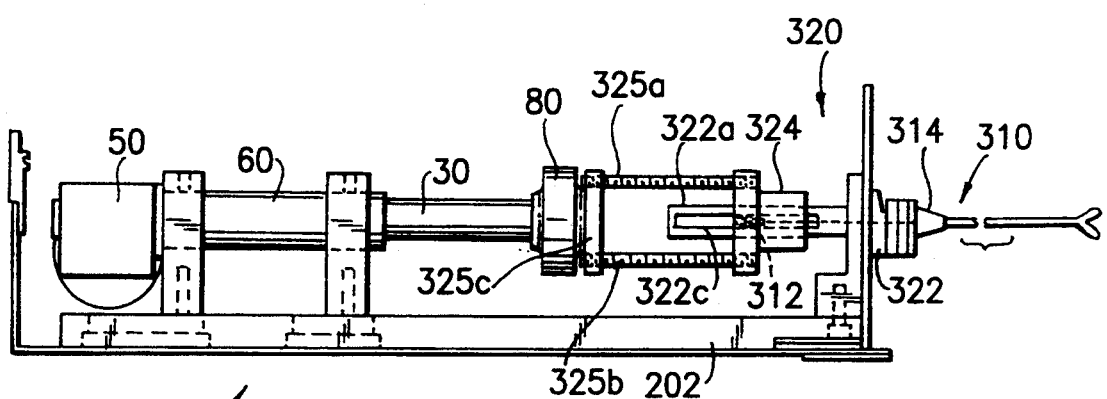
FIG. 5 is side elevational view of another embodiment of the remote control apparatus of the invention having coupling means for coupling to the distal end of separable biopsy forceps.
Figure 6:
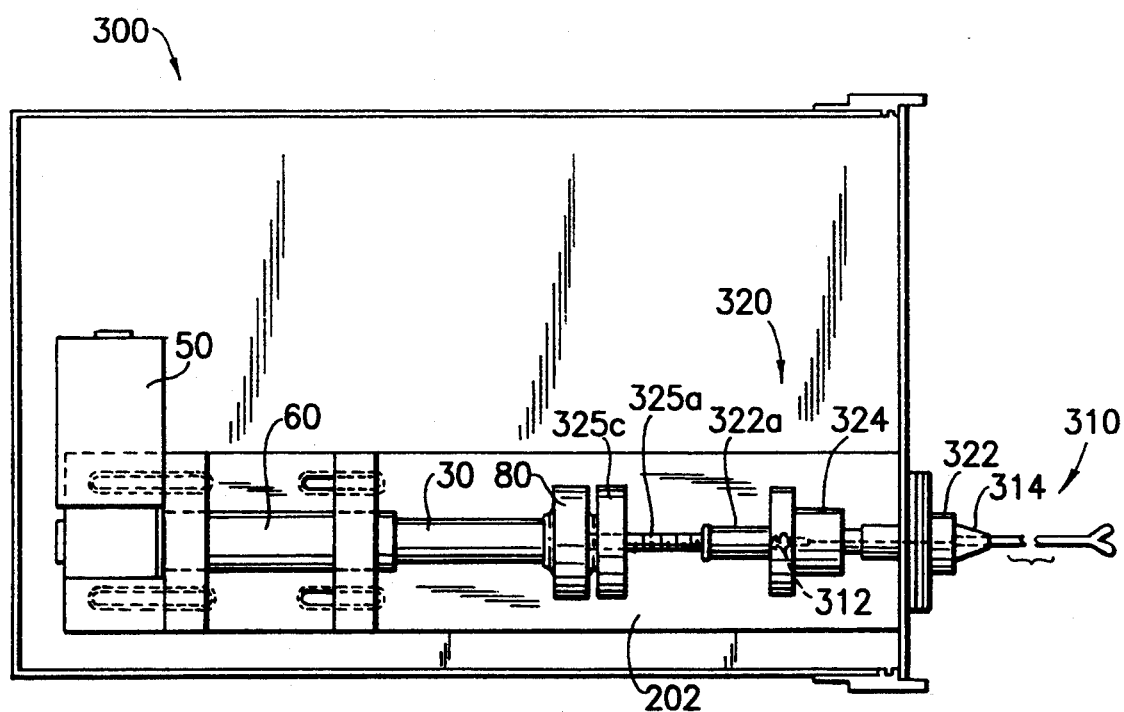
FIG. 6 is a top plan view of the embodiment of FIG. 5.
Figure 5A:
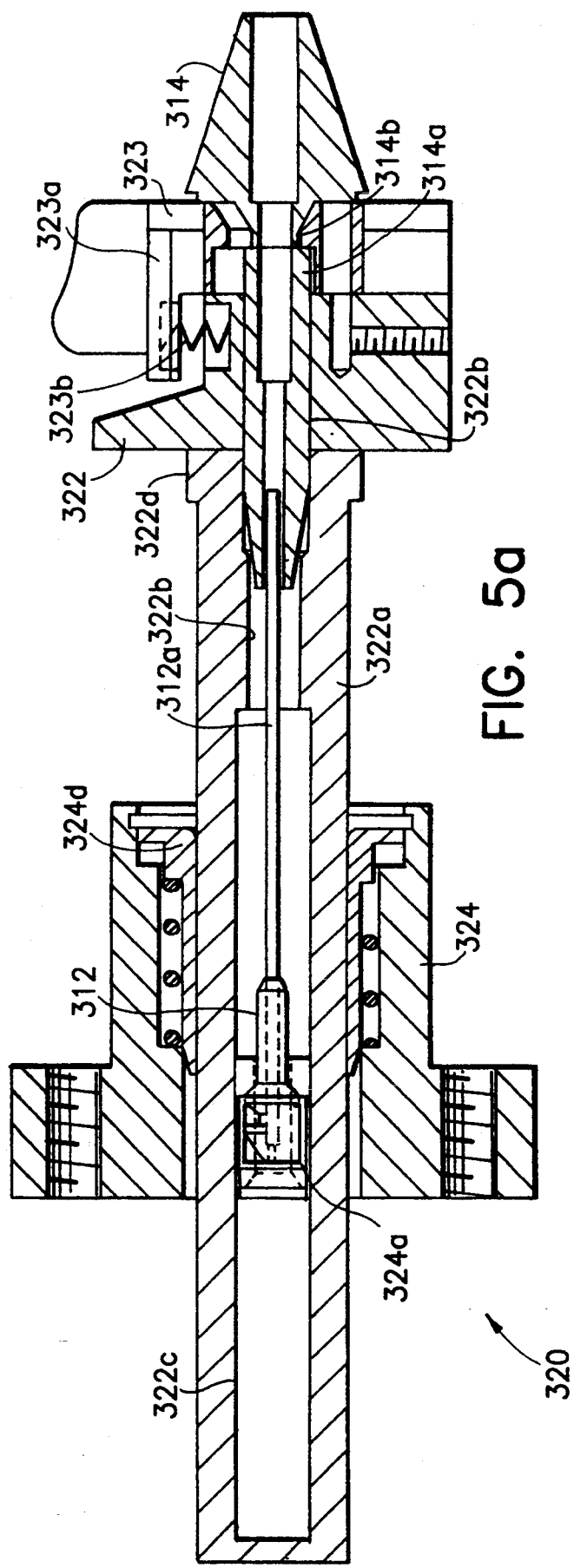
FIG. 5a is an enlarged view of a portion of FIG. 5.
Figure 6A:
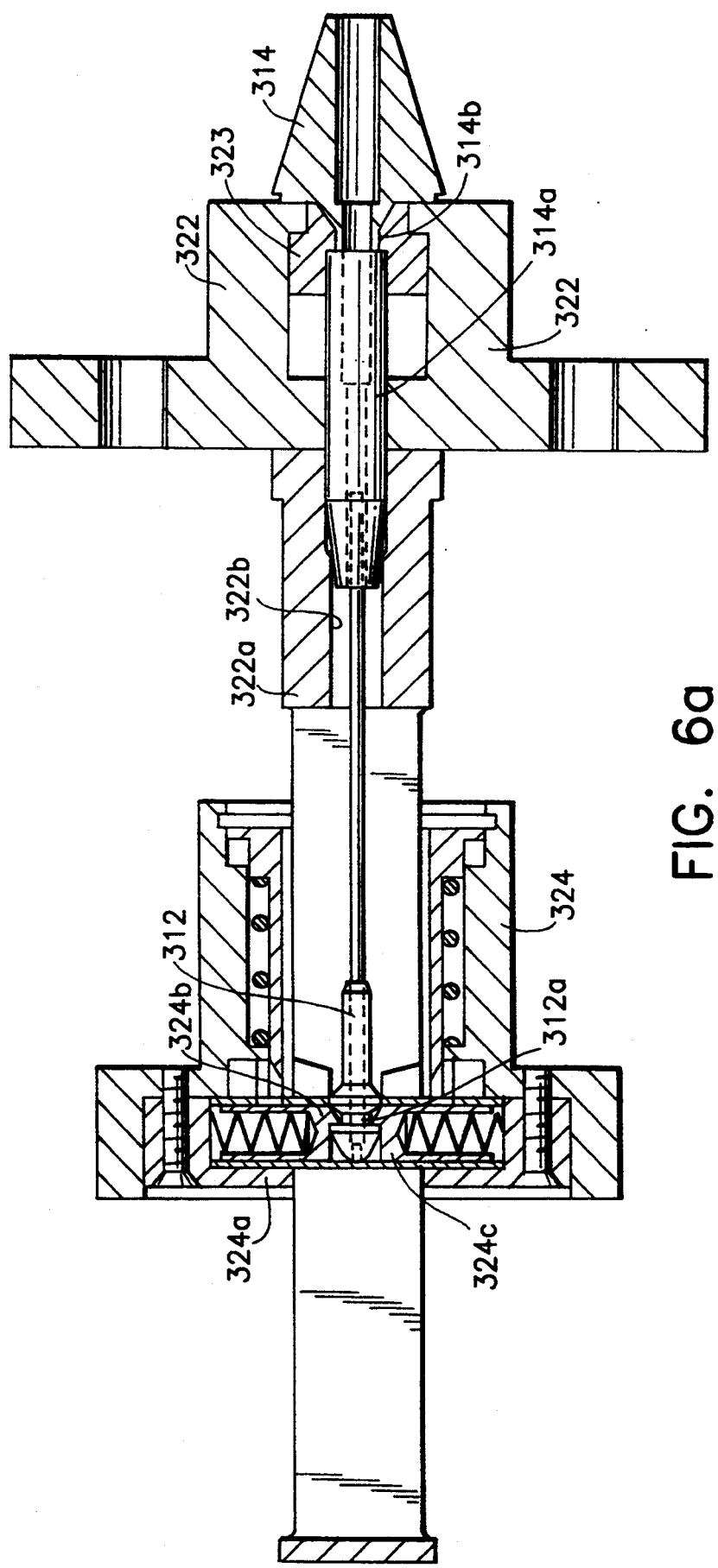
FIG. 6a is an enlarged view of a portion of FIG. 6.

In this embodiment, the coupling device 320 is substantially the same as that shown in FIGS. 5 and 6 and is coupled at beam 325c to load cell 80. The driving means comprises an hydraulic or pneumatic cylinder 660 having an internal piston (not shown) coupled to a piston rod 630. The piston rod 630 is coupled to the load cell 80. Cylinder 660 is provided with a pair of fluid ports 662, 664 through which fluid (air, hydraulic fluid, etc) flows to move the piston (not shown) in either of two directions. Fluid ports 662, 664 are respectively coupled to flow metering valves 642, 644 which in turn are coupled by a fluid conduit 652 to a source of pressurized fluid 650. A pressure indicator 655 is preferably included in series between the fluid source 650 and the valves 642, 644. The flow metering valves 642, 644 are controlled by controller 640 which receives input from user interface 670 and load cell 80. It will be appreciated that a pressure transducer could be utilized in lieu of the load cell.

5. Controllers

5A. Electric Motor Controller

Figure 13:
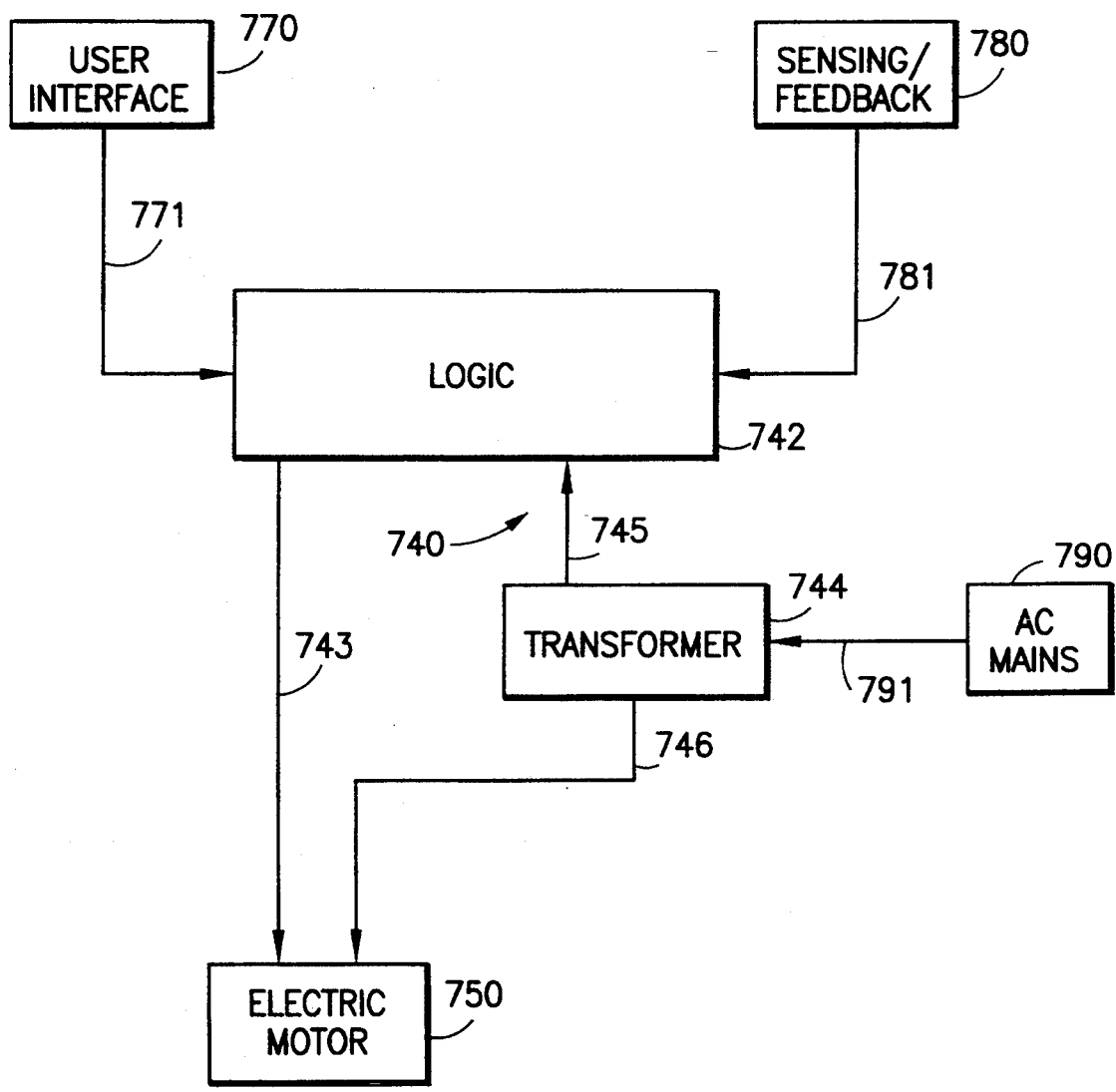
FIG. 13 is a block diagram of a controller circuit for an electric drive means.

FIG. 13 shows one embodiment of a controller 740 for use with an electric motor power source 750 such as the electric motors shown in FIGS. 7-10 or a linear actuator such as shown in FIGS. 3-6. As seen in FIG. 13, the controller 740 includes a transformer 744 coupled to the AC mains 790. Transformer 744 provides a reduced voltage (typically 12 V) for use by logic circuit 742 and the electric motor 750. Those skilled in the art will realize that the "transformer" 744 will usually include rectifier means to convert the AC source to DC. As such, the transformer 744 provides a 12 V DC signal via connection 745 to logic circuit 742 and via connection 746 to electric motor 750.

Logic circuit 742 receives inputs from both the user interface 770 which is described in detail below and from the sensing/feedback means 780 which is also described in detail below. The user interface 770 typically provides input for commanding the controller 740 to perform at least two functions (e.g., open jaws, and close jaws). The sensing/feedback means 780 typically provides an electric signal related to the position and/or force exerted by the drive means on the pull wire(s) in response to the electric motor 750 and in response to coiling and uncoiling of the coil carrying the pull wire as it is extended through the endoscope. The logic circuit controls the motor 750 through connection 743. Those skilled in the art will appreciate the many ways in which motor 750 may be controlled.

FIGS. 13a-13e illustrate the basic functions of the logic circuit 742 of the controller 740. In a preferred embodiment, the logic circuit performs four functions. In addition to the (1) open and (2) close jaws functions, a (3) couple/uncouple function is designed to bring the coupling means into a position whereby the forceps may be coupled to or decoupled from the invention, and a (4) "home" or "idle" function which is a closed position with a minimal force provided to hold the jaws of the forceps closed so that the forceps can be guided to and from the biopsy site by the surgeon.

Figure 13A:
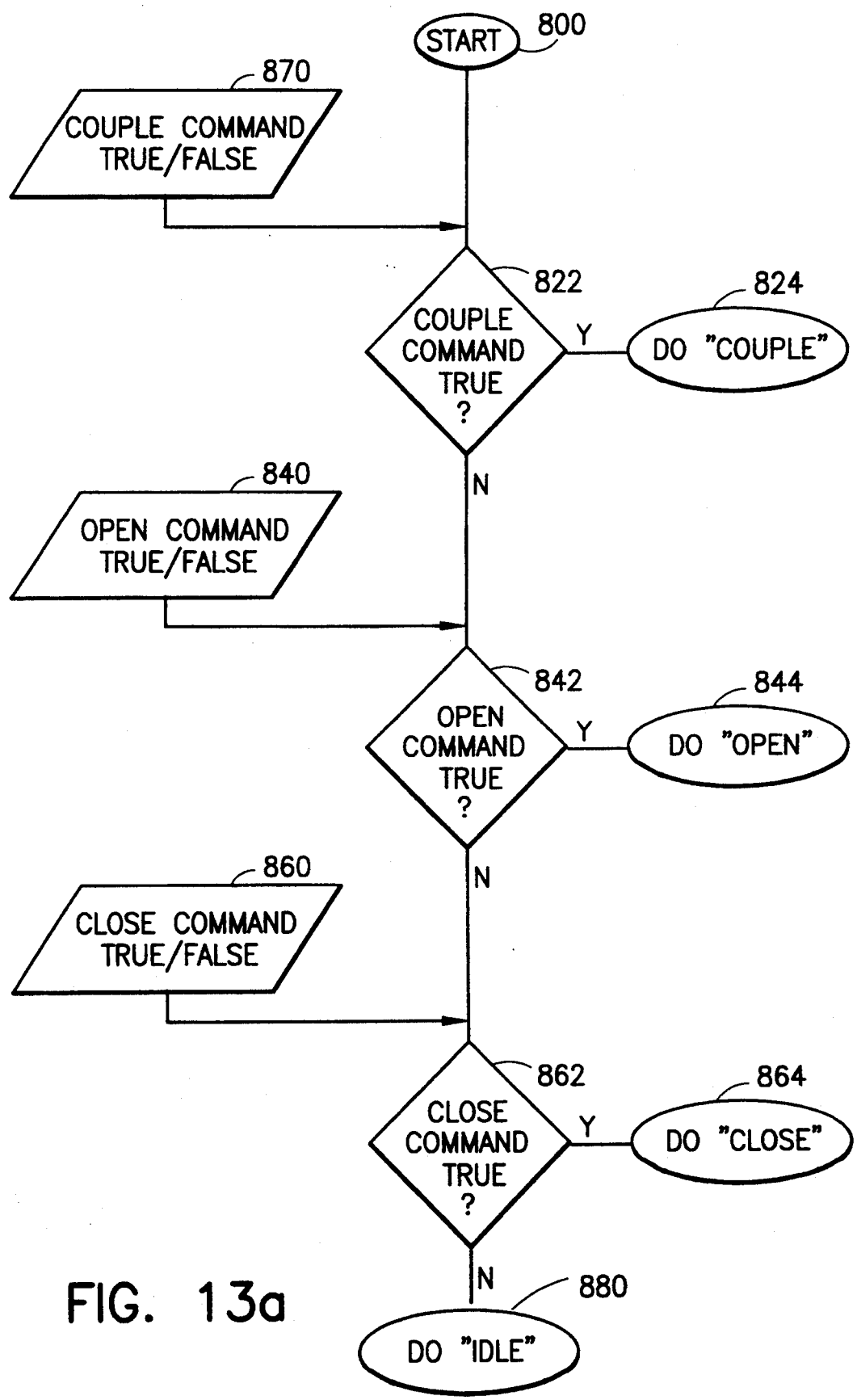
FIGS. 13a–13e are flow charts for the controller circuit of FIG. 13.
Figure 13B:
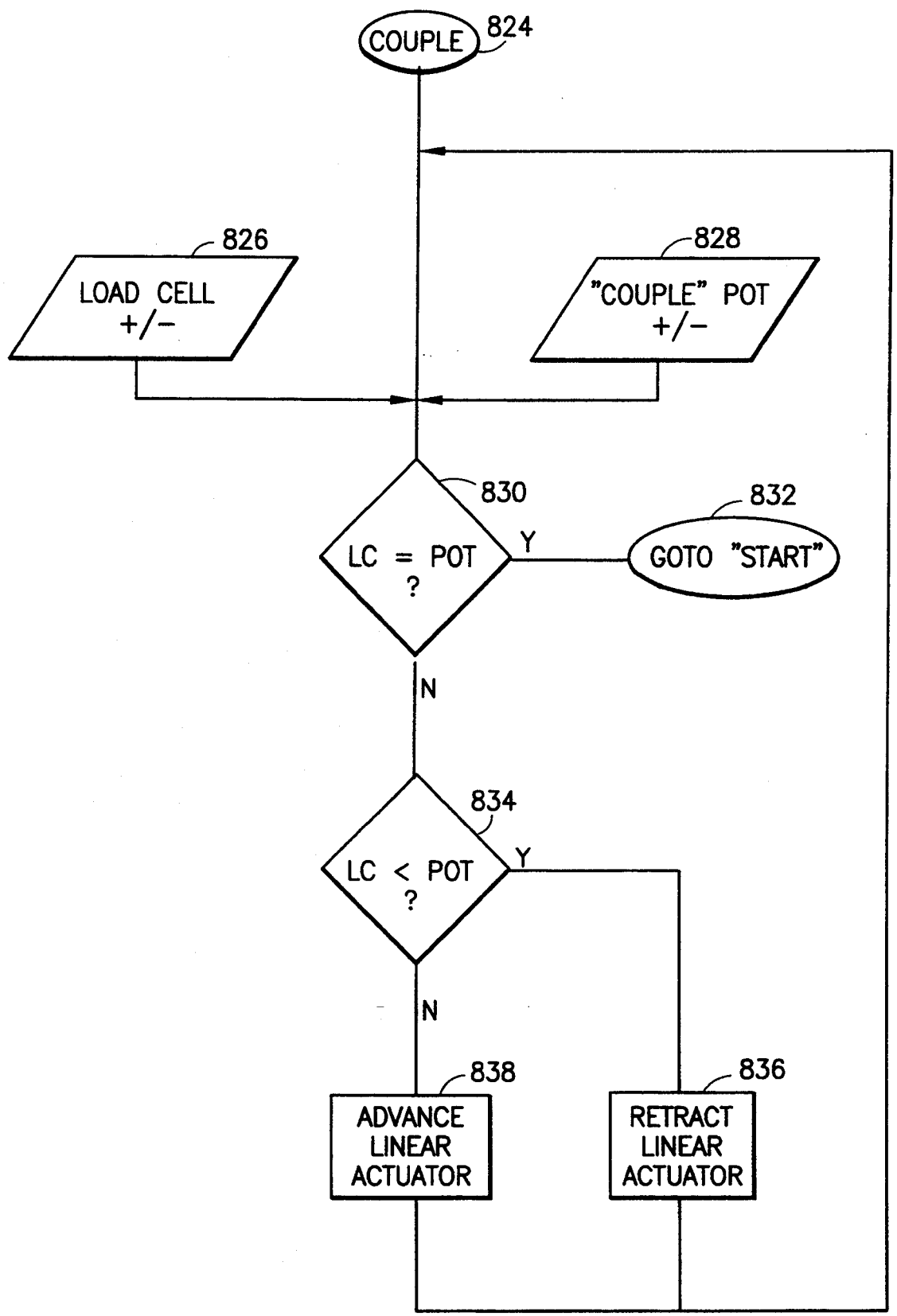

The controller is started at 800 either by a command from the user interface or by a separate power switch. If a couple/uncouple command 820 is detected at 822, the controller performs the necessary function at 824 to put the drive means 60 and thus the coupling device 20 into a position whereby the endoscopic forceps device can be coupled or uncoupled from the invention. FIG. 13b shows one example of how this can be done. At the start of the couple/uncouple function 824, the controller compares the load on the load cell 826 to a reference value as set by a potentiometer 828 or otherwise available to the logic circuit (e.g. in ROM or the like). If the values are the same as compared at 830, the controller returns at 832 to the start 800 (FIG. 13a) meaning that the coupling device is already in the couple/uncouple position. If, the actual position of the drive means is not equal to the reference position, the controller checks at 834 to see if the actual position is greater or less than the reference position and incrementally advances or retracts the drive means at 838 or 836, respectively, and compares the values again at 830. This process is repeated until the drive means is advanced or retracted to the appropriate position as determined at 830, at which time the controller returns (832) to start 800 (FIG. 13a).

Figures 1, 13C:
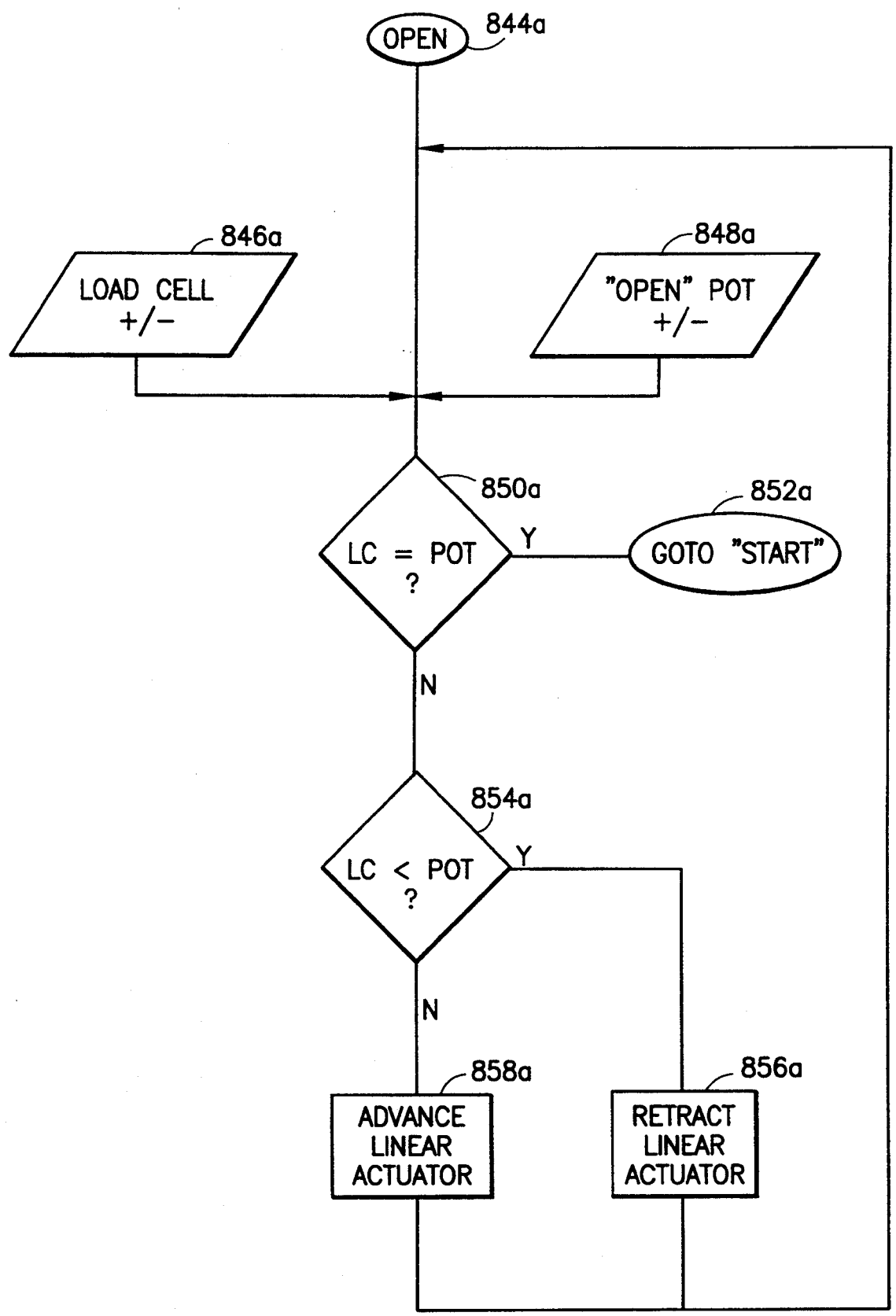
Figures 2, 13C:
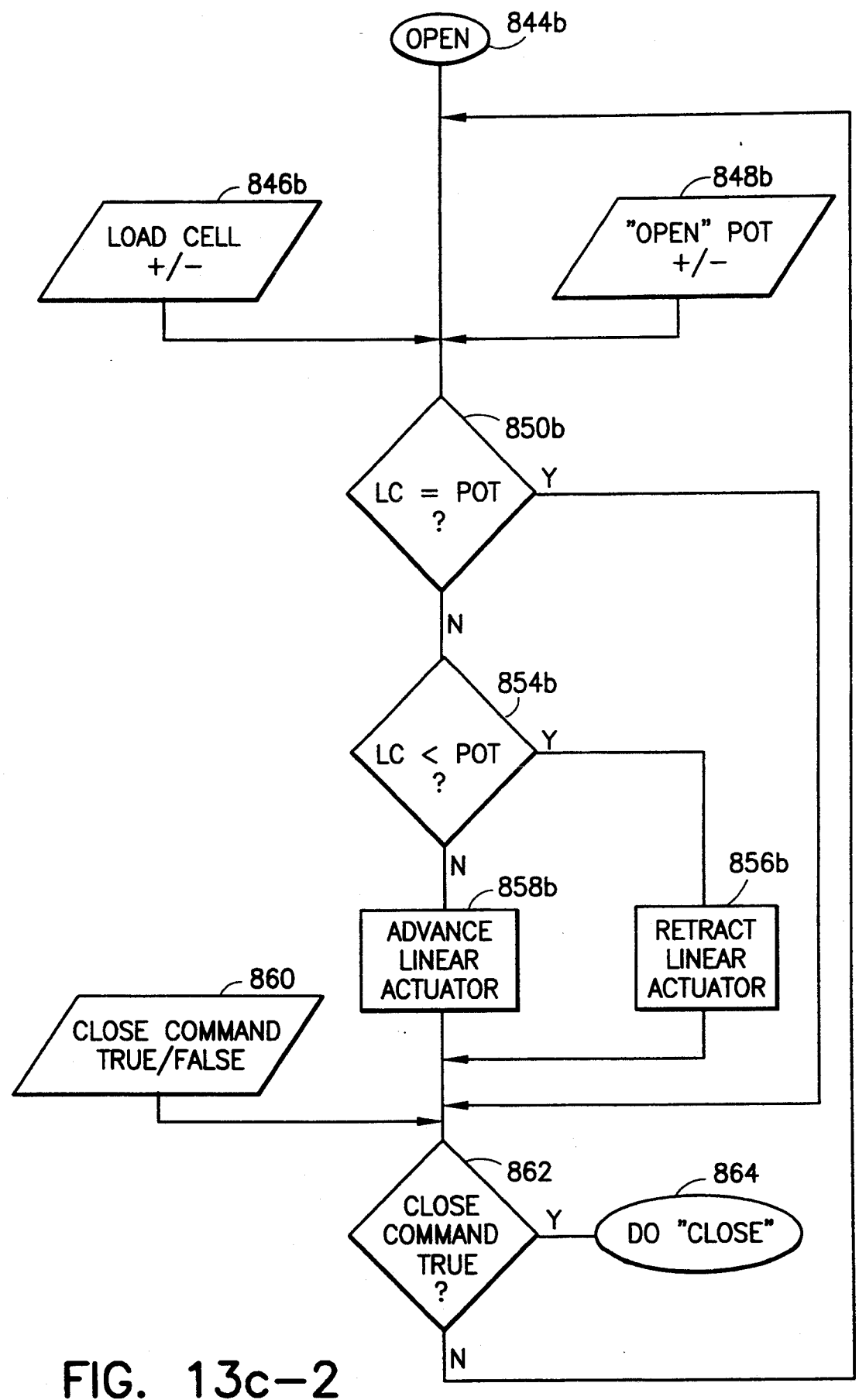

If the open command 840 is detected at 842, the controller performs the necessary function at 844a or 844b to put the drive means 60 and thus the coupling device 20 into a position whereby the forceps are open. FIG. 13c-1 and 13c-2 show two examples of how this can be done. Turning to FIG. 13c-1, at the start of the open function 844a, the controller compares the force exerted on the pull wires as determined by a load cell 846a to a reference value as set by a potentiometer 848a. If the values are the same as compared at 850a, the controller returns at 852a to the start 800 (FIG. 13a), meaning that the forceps are already in the open position. If, the load is not equal to the reference value, the controller checks at 854a to see if it is greater or less than the reference and incrementally advances or retracts the drive means at 858a or 856a, respectively, and compares the values again at 850a. This process is repeated until the drive means is advanced or retracted to apply the appropriate force, at which time the controller returns to start 800 (FIG. 13a). It will be appreciated that in this embodiment, if the open command is not maintained, the controller will cause the apparatus to enter the "idle" mode (see FIG. 13a).

A second embodiment of the "open" command is seen with reference to FIG. 13c-2. At the start of this open function 844b, the controller compares the force exerted on the pull wires as determined by a load cell 846b to a reference value as set by a potentiometer 848b. If the force is not equal to the reference, the controller checks at 854b to see whether it is greater or less than the reference and incrementally advances or retracts the drive means at 858b or 856b. Then, the controller determines at 862 whether a close command has been received at 860. If yes, the controller goes to the close command at 864. If not, the controller returns to 850b to compare the load cell and control values, and to cycle back through until the drive means is advanced or retracted to apply the appropriate force as determined at 850b. If the values are the same as compared at 850b, the controller goes to 862 to check whether the close command of 860 has been received. As described above, if the close command is not received, the controller continues by returning and comparing the load cell and control values. It will be appreciated that this embodiment of the "open" command locks the jaws of the endoscopic instrument in an open position until the close command is given.

Figure 13D:
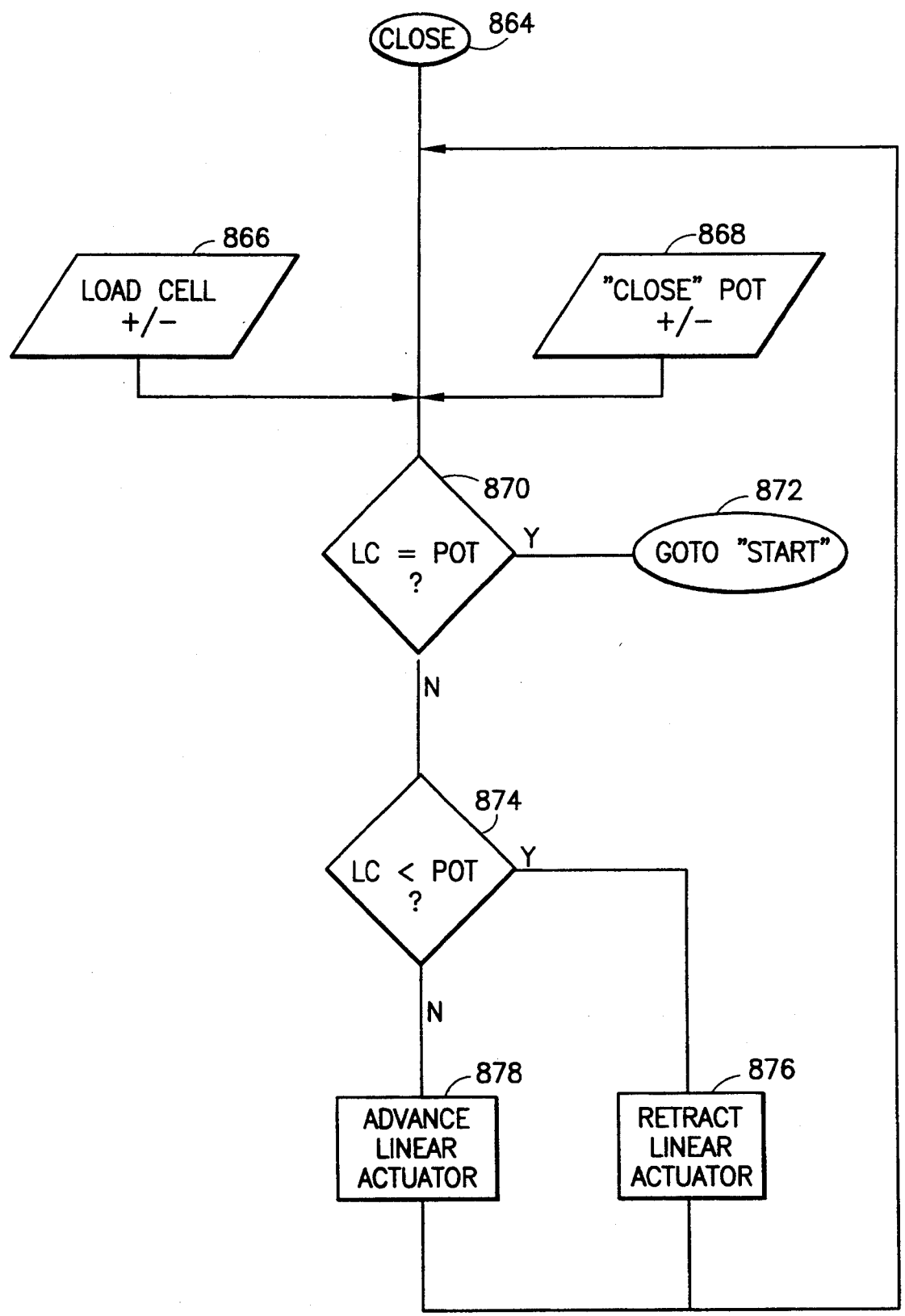

If the close command 860 is detected at 862, the controller performs the necessary function at 864 to put the drive means 60 and thus the coupling device 20 into a position whereby the forceps are closed. FIG. 13d shows one example of how this can be done. At the start of the open function 864, the controller compares the load on the load cell 866 to a reference value as set by a potentiometer 868. If the values are the same as compared at 870, the controller returns at 872 to the start 800 (FIG. 13a) meaning that the forceps are already in the closed position. If, the load is not equal to the reference, the controller checks at 874 to see if the actual load is greater or less than the reference value and incrementally advances or retracks the drive means at 878 or 876, respectively, and compares the values again at 870. This process is repeated until the drive means is advanced or retracted to the appropriate position at which time the controller returns to start 800 (FIG. 13a).

Figure 13E:
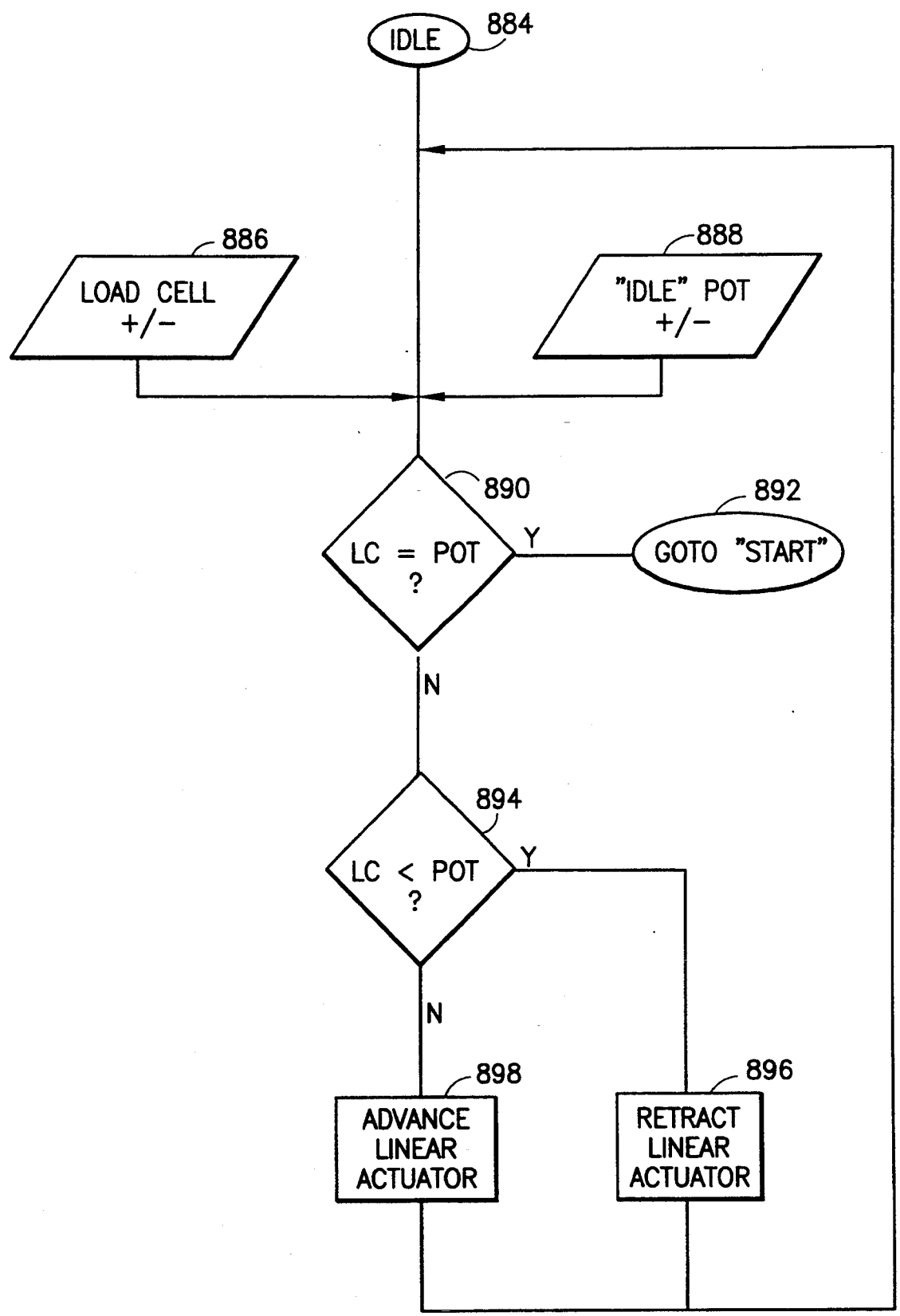

If no command is given, the controller puts the forceps into a "home" or "idle" position which is a closed position with a minimal force holding the jaws of the forceps closed so that the foreceps can be guided to the biopsy site by the surgeon. FIG. 13e shows one example of how this can be done. At the start of the home or "idle" function 884, the controller compares the force (load) on the load cell 886 to a reference value as set by an "idle" potentiometer 888. If the values are the same as compared at 890, the controller returns at 892 to the start 800 (FIG. 13a) meaning that the forceps are already in an idle position. If, the load is not equal to the reference, the controller checks at 894 to see if the actual load is greater or less than the reference value and incrementally advances or retracts the drive means at 898 or 896, respectively, and compares the values again at 890. This process is repeated until the drive means is advanced or retracted to the appropriate position at which time the controller returns to start 800 (FIG. 13a). As discussed above, in the idle (default) position, the apparatus of the invention dynamically senses the force on the pull wire(s) of the endoscopic instrument and constantly makes corrections in order to maintain the idle position force.

Figure 13F:
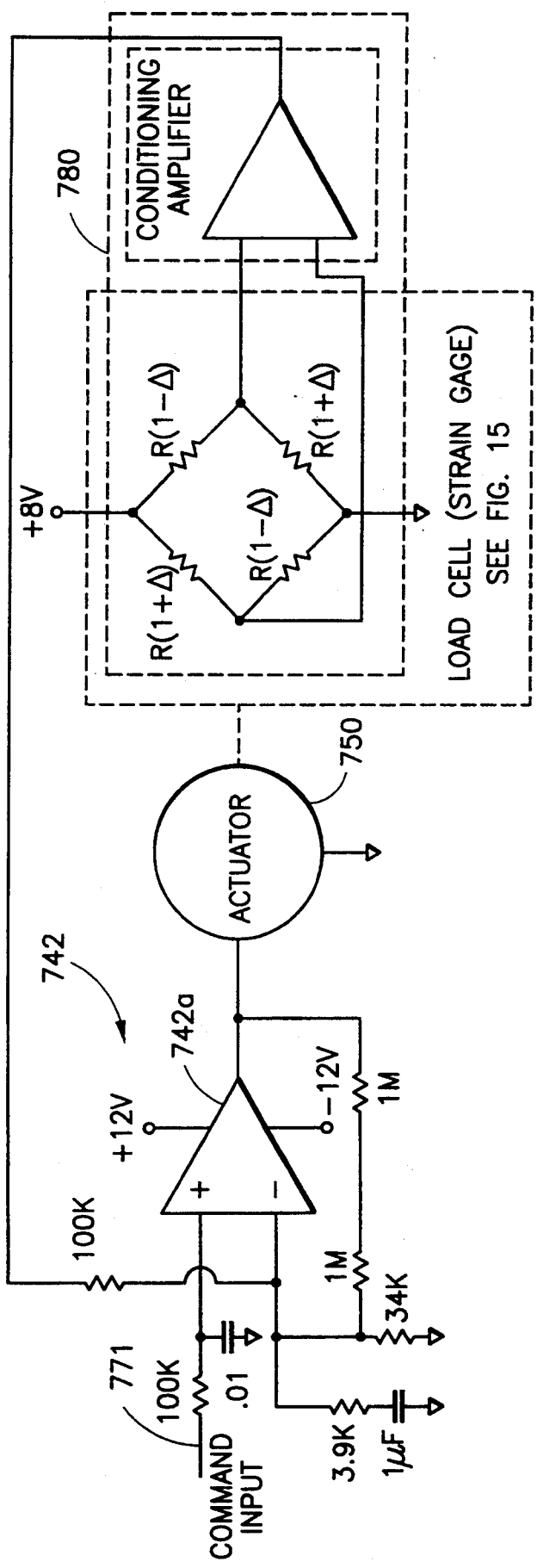
FIG. 13f is a schematic diagram of one implementation of the controller of FIG. 13.

FIG. 13f shows a schematic diagram of one possible embodiment of a controller as described above. Here the logic circuit is a simple comparator 742a which compares voltage supplied at its negative input from a strain gage (described below in FIG. 15) with voltage supplied at its positive input from a user interface (described below in FIG. 18). Those skilled in the art will appreciate that the various resistors and capacitors coupled to comparator 742a aid in providing an output signal appropriate to control electric motor 750.

It will be appreciated that the schematic illustration described above with reference to the operation of the controller is but one manner in which the controller may be constructed. Moreover, a similar electronic controller circuit could be applied through the use of solenoids, etc. to different power sources such as hydraulic/pneumatic power sources.

5C. Pneumatic/Hydraulic Drive Controller

Figure 14:
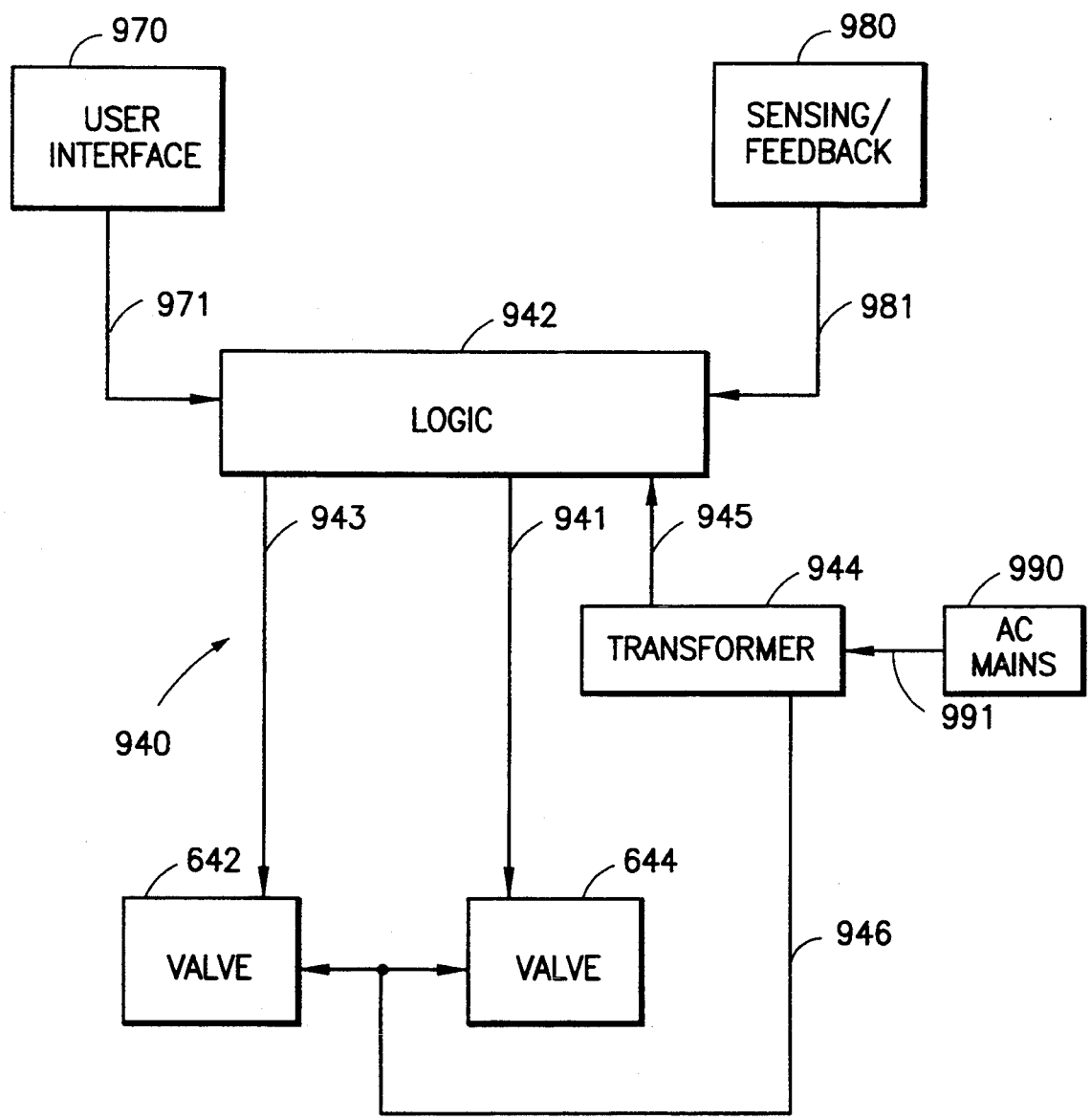
FIG. 14 is a block diagram of a controller circuit for an hydraulic/pneumatic drive means.

FIG. 14 shows one embodiment of a controller 940 for use with an hydraulic or pneumatic power source such as the cylinder 660 shown in FIGS. 11 and 12. As seen in FIG. 14, much of the controller is the same as the controller described above. The controller 940 includes a transformer 944 coupled to AC mains 990. Transformer 944 provides a reduced voltage (typically 12 V) for use by logic circuit 942 and flow metering valves 642, 644. Those skilled in the art will realize that the "transformer" 944 will usually include rectifier means to convert the AC source to DC. As such, the transformer 944 provides a 12 V DC signal via connection 945 to logic circuit 942 and via connection 946 to valves 642, 644.

Logic circuit 942 receives input from the user interface 970 which is described in detail below and from the sensing/feedback means 980 which is also described in detail below. The user interface 970 typically provides input for commanding the controller 940 to perform at least two functions (e.g., open jaws, and close jaws). The sensing/feedback means 980 typically provides an electric signal related to the position and/or force exerted by the drive means. The logic circuit controls the opening and closing of the valves 642, 644 through electrical connections 943,941.

Those skilled in the art will appreciate that the position of a piston in the cylinder of a pneumatic or hydraulic drive means can be readily adjusted by operation of valves as shown for example in FIGS. 11 and 12, and that the force exerted by the piston rod can be adjusted by varying the pressure within the cylinder. Those skilled in the art will also recognize that a diaphragm or other pressure regulator could be utilized.

The functional operation of this embodiment of the controller is substantially the same as the controller described above with reference to FIGS. 13a–13e.

6. Sensing/Feedback Means
6A. Load Cells

Figure 15:
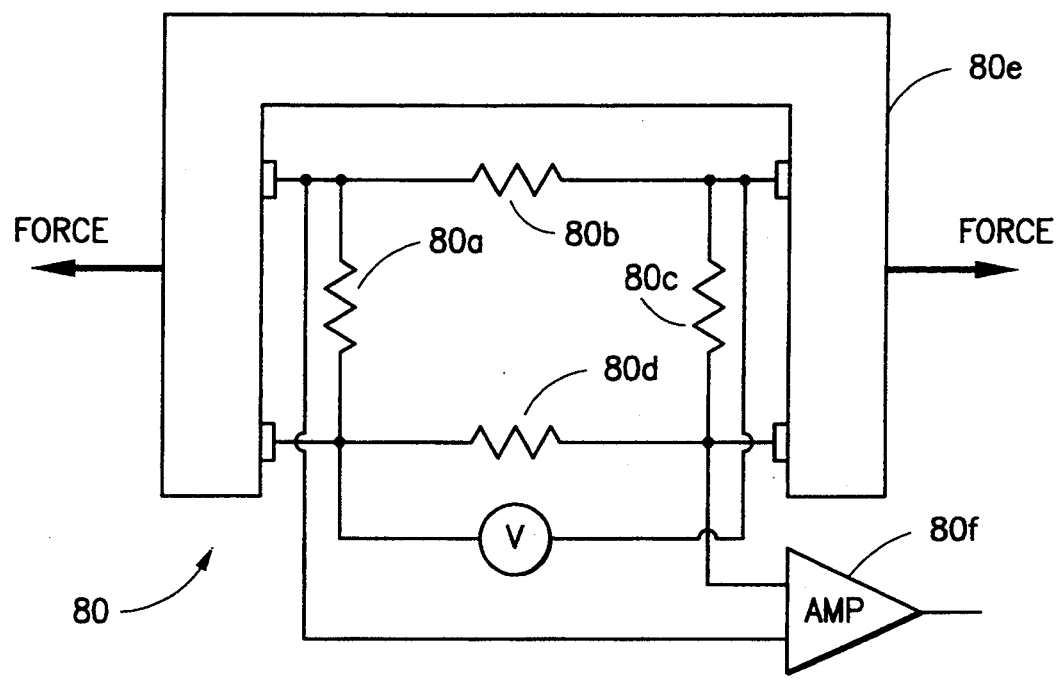
FIG. 15 is a schematic view of a load cell sensing-/feedback device.

The sensing/feedback means disclosed thus far is a load cell such as a Wheatstone bridge network strain gage. FIG. 15 shows a schematic diagram of such a load cell or strain gage. Those skilled in the art will understand that a load cell or strain gage 80 is composed of a Wheatstone bridge network 80a–80d, opposite arms of which are mechanically bonded to a structural member 80e whose stress or strain is being measured. The strain gage elements 80a–80d are made of fine wires which change their resistances as they are stretched or compressed. While these changes are small, because they occur in opposite arms of the bridge they are magnified. Moreover, a conditioning amplifier 80f, coupled to the network provides a useful signal related to stress or strain.

As used herein, the strain gage is advantageously placed at some point between the drive means and the coupling means, as shown for example in FIGS. 3–6 and 8–12. The output from amplifier 80f is coupled to the controller as shown schematically in FIGS. 13 and 14.

6B. Endpoint Spring/Switch

Figure 16:
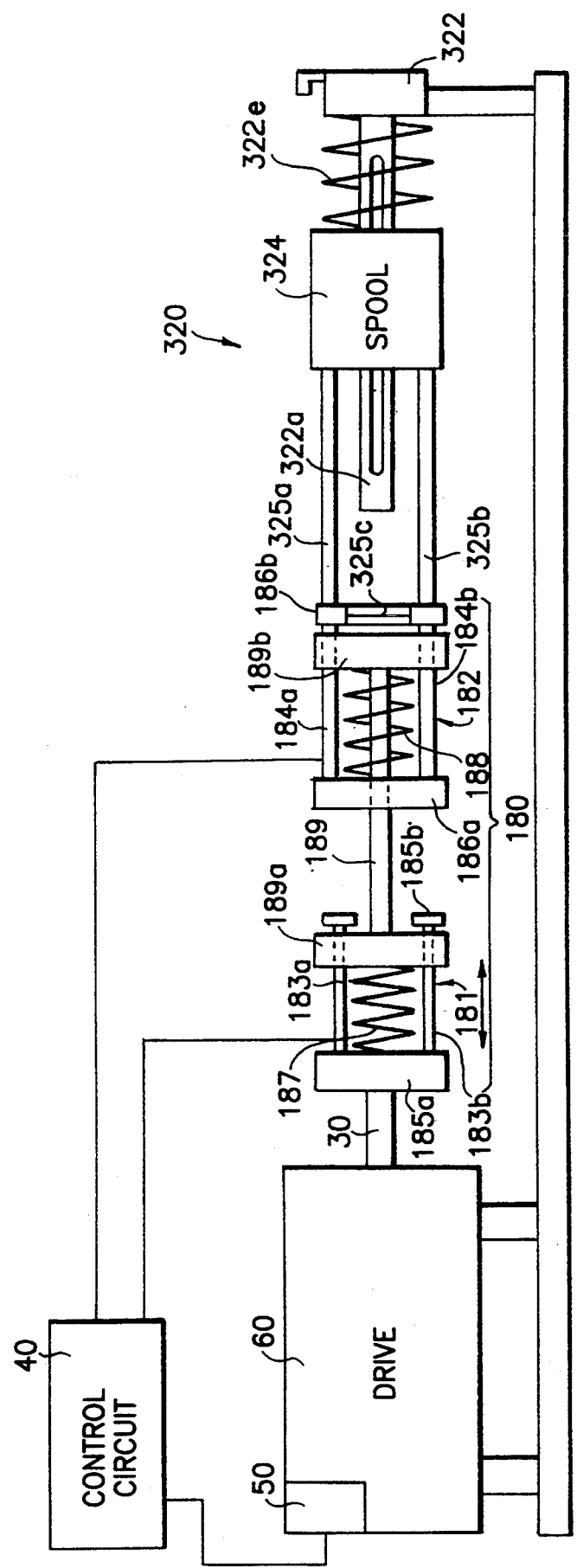
FIG. 16 is a side elevation view of a spring controlled force limiting coupling between the drive means and the coupling device.

Another type of sensing/feedback means which can be used with the invention is shown in FIG. 16 in the context of coupling and driving means similar to those shown in FIGS. 5 and 6.

FIG. 16 shows a sensing/feedback means 180 which includes a pair of springs 187, 188 and a pair of switches 185a, 186a. Switch 185a is mounted on linkage 30 which is coupled to drive means 60. A pair of slip rods 183a, 183b extend from the switch 185a and terminate with a stop 185b. A switch activator 189a is slip mounted on the slip rods 183a, 183b and is spring biased towards the stop 185b by a spring 187 between it and the switch 185a. Switch 186a is provided with a similar pair of slip rods 184a, 184b terminating with a similar stop 186b. Stop 186b is coupled to rods 325a and 325b either directly, or optionally (as shown) via beam 325c of the coupling device 320 (described in detail above with reference to FIGS. 5 and 6). A switch activator 189b is slip mounted on rods 184a, 184b and is biased towards the stop 186b by a spring 188. The two switch activators 189a, 189b are coupled by a central rod 189.

From the foregoing description and with reference to FIG. 16, those skilled in the art will appreciate that when the drive means moves linkage 30 forward (typically to open the jaws of the forceps), switch activator 189b will abut stop 186b while switch 185a is moved against spring 187 towards switch activator 189a. When spring 187 is fully compressed, switch activator 189a will activate switch 185a indicating that the forward force of the drive means is substantially equal to the force required to compress spring 187. By knowing the specifications of spring 187, a value can be assigned to the force applied by the drive means at the time switch 185a is activated.

Similarly, when the drive means 60 moves linkage 30 rearward (typically to close the jaws of the forceps), switch activator 189a will abut stop 185b while switch activator 189b is moved against spring 188 towards switch 186a. When spring 188 is fully compressed, switch activator 189b will activate switch 186a. As with spring 187 and switch 185a, a value can be assigned to the force applied in the rearward direction when switch 186a is activated.

FIG. 16 also shows a third spring 322e mounted between spool 324 and coil coupling 322 which biases the spool rearward to an "idle position" where a slight force keeps the forceps jaws closed.

6C. Spring Loaded Variable Resistor

Figure 16A:
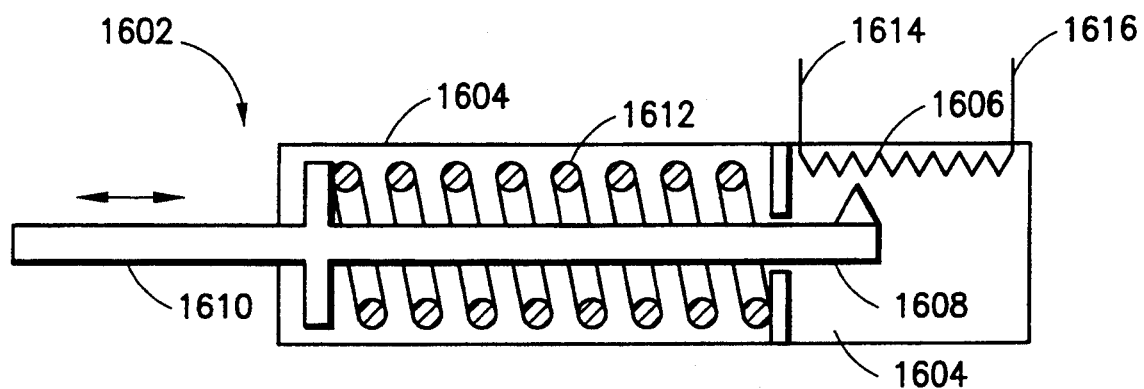
FIG. 16a is a schematic diagram of a spring loaded variable resistor sensing/feedback device.

FIG. 16a shows another type of sensing feedback means 1602 with a variable resistor 1604 having a wire winding 1606 and a sliding contact 1608. The sliding contact 1608 is coupled to a shaft 1610 biased to an extreme position by a spring 1612. As the shaft 1610 is moved against spring 1612, the resistance across contacts 1614, 1616 changes. Recognizing that linear displacement of the sliding contact 1608 changes the resistance across contacts 1614, 1616 while at the same time changing the force exerted by spring 1612, the amount of force exerted on shaft 1610 can be related to a particular resistance measured across contacts 1614, 1616.

6D. Spring Loaded LVDT

Figure 16B:
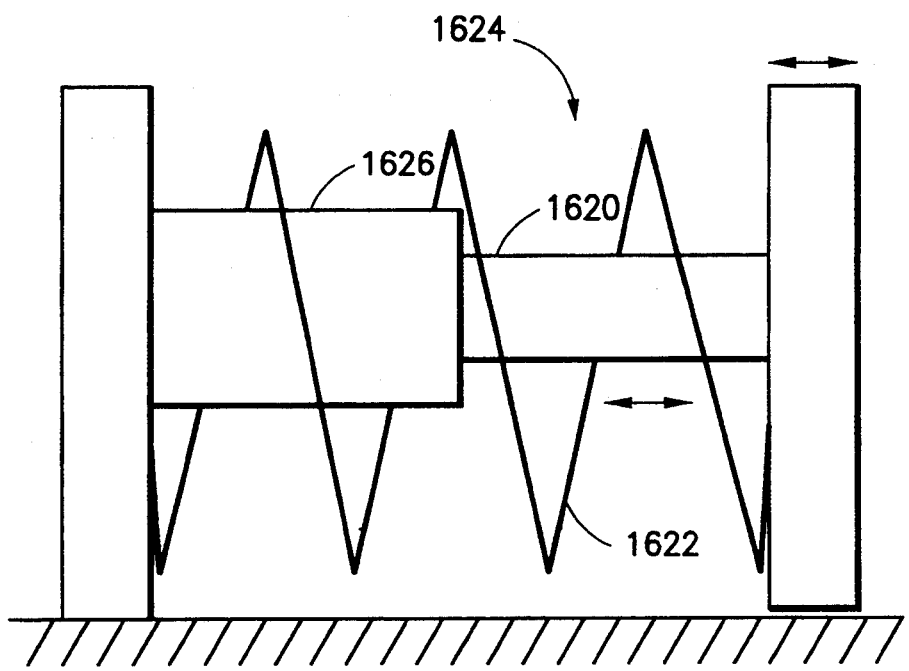
FIG. 16b is a schematic side elevation diagram of a LVDT sensing/feedback device.

FIG. 16b is an alternate embodiment of a spring biased position sensor used as a sensing/feedback means. In this embodiment, the position sensor is an LVDT 1624 (linear variable displacement transducer) such as the LD200 or LD 200 Series from Omega Engineering, Inc., One Omega Drive, Stamford, Conn. 06906. The LVDT includes a body (cylinder) 1626 containing primary and secondary transformer coils (not shown) and a transformer core (piston) (not shown) coupled to a plunger 1620 which moves the core through the body 1626. The primary coil is AC powered and the secondary coil(s) produce a variable output voltage depending on the position of the plunger (transformer core).

This embodiment operates in a manner similar to the embodiment described above in FIG. 16a. By providing a spring 1622 with a known spring constant and noting the position of the plunger 1620 as determined by the signal from the secondary coil(s) of the LVDT, the amount of force exerted on the plunger can be calculated.

6E. Current Sensing Circuit

Figure 16C:
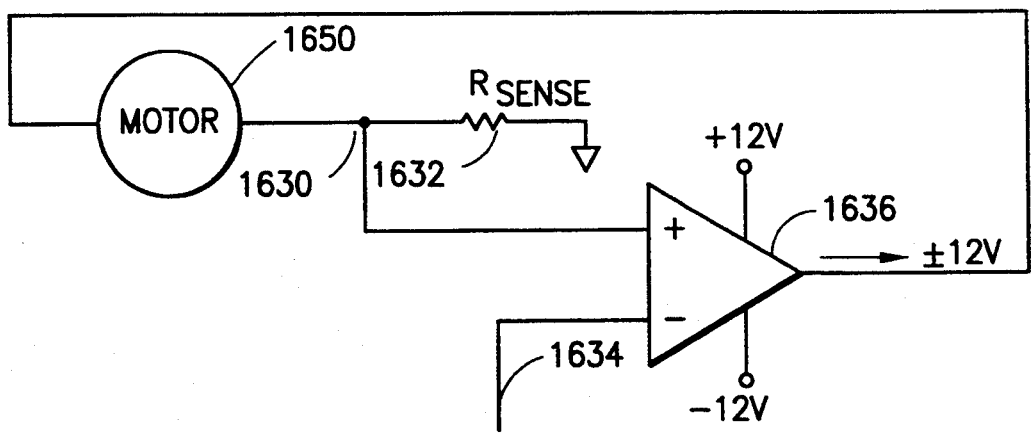
FIG. 16c is schematic electrical diagram of a current sensing/feedback device.

FIG. 16c shows one embodiment of a current sensing sensing/feedback means for use with a non-locking drive means. The current sensing device shown in FIG. 16c is based on a comparison of the low voltage at the common point 1630 between motor 1650 and low impedance resistor 1632 with a reference voltage given as a command signal 1634.

Those skilled in the art will appreciate that the output (typically ±12 volts) of comparator/amplifier 1636 drives motor 1650 and that the voltage at common point 1630 is very small, approximately 0.2 volts. By supplying a reference voltage command signal 1634 of approximately +2 volts, comparator/amplifier 1636 begins feeding maximum voltage to motor 1650. As the load on the motor increases (force applied to the pull wire(s)), current flowing through the motor increases as does the voltage at common point 1630. This causes the comparator/amplifier to reduce its output, holding the motor in a state of constant predetermined load (constant predetermined force exerted on the pull wire(s)).

6F. Pressure Transducer

Figure 17:
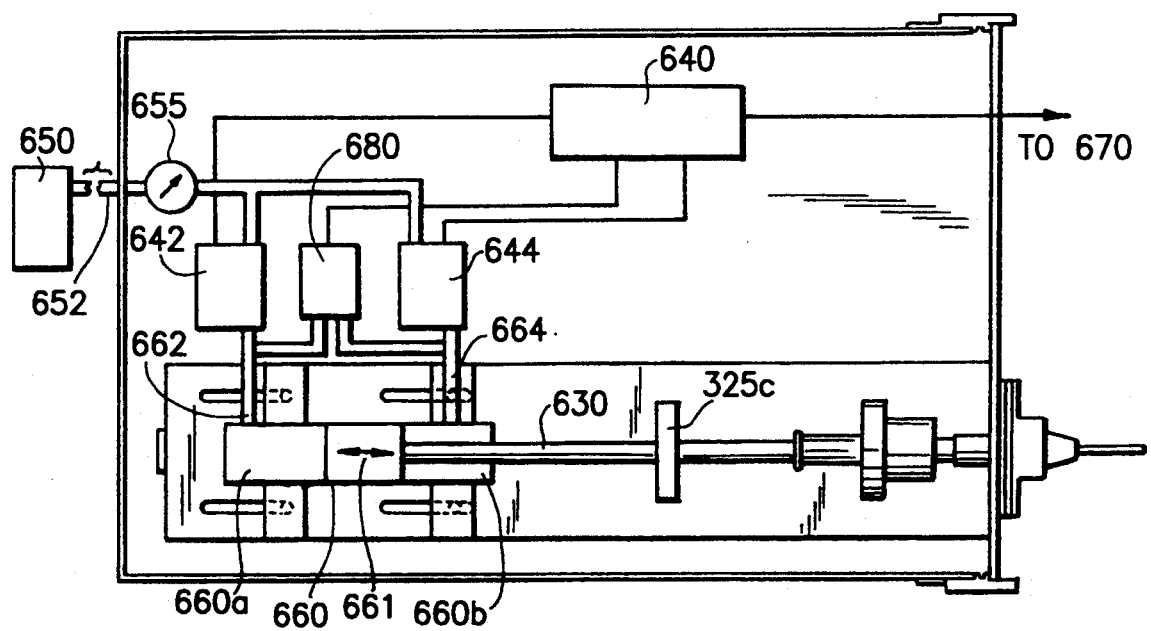
FIG. 17 is a block diagram of a pressure transducer for use with a hydraulic/pneumatic drive means.

FIG. 17 shows a pressure transducer sensing/feedback means 680 for use with a hydraulic or pneumatic cylinder 660 (described above in FIGS. 11 and 12. Cylinder 660 is provided with a piston 661 flanked by two fluid pressure chambers 660a, 660b which are respectively coupled to conduits 662, 664. Flow metering valves 642, 644 feed/drain pressure fluid to pressure chambers 660a, 660b in order to move piston 661 forward or backward as shown by the arrows in FIG. 17.

Pressure transducer 680 is a differential pressure transducer which senses the difference in fluid pressure as between conduits 642, 644, thereby determining the forward or rearward force presently exerted on piston 661. Transducer 680 feeds a signal to the controller 640 which is also coupled to the fluid metering valves 642, 644. In response to a command from interface 670, the controller controls valves 642, 644 until the signal from transducer 680 reaches an appropriate level.

It will be appreciated that the force exerted on piston 661 is transferred to the pull wire(s) of the forceps by linkage 630.

7. User Interfaces
7A. Switch Control

Figure 18:
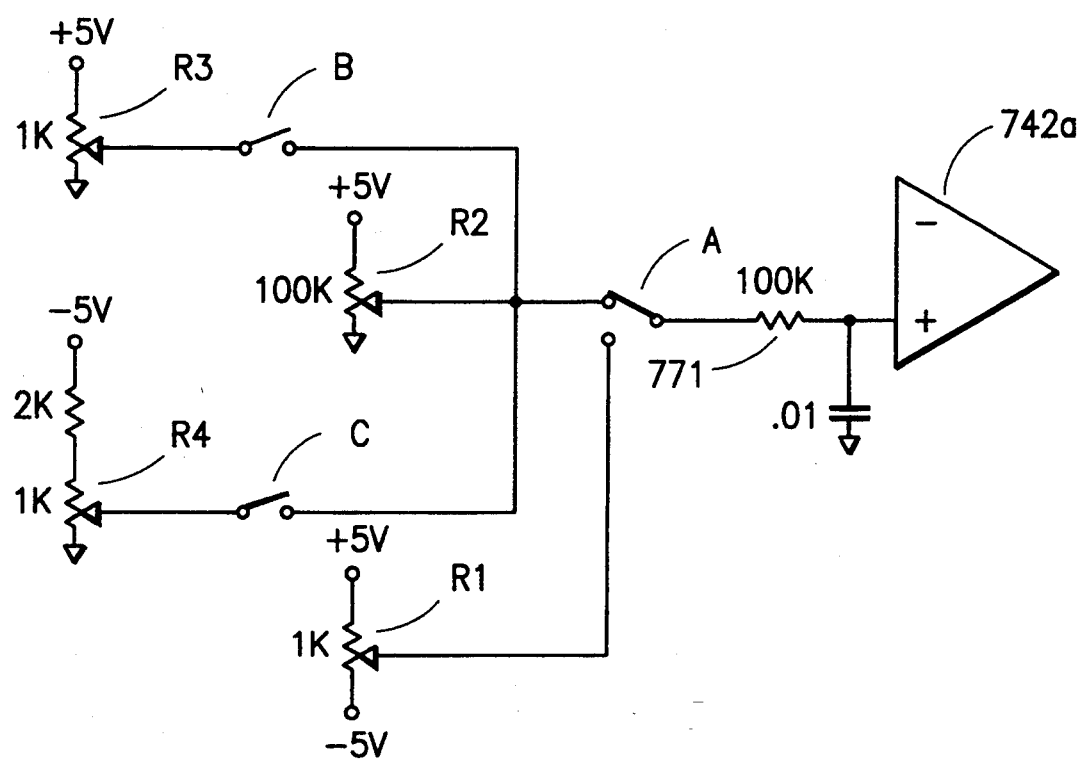
FIG. 18 is a schematic diagram of a control circuit for a foot or hand operated switch.

FIG. 18 shows a resistor switching circuit for providing a command input to the comparator 742a of FIG. 13e. A first switch A, when closed, couples the positive input of the comparator 742a to a voltage determined by resistor R1 for putting the coupling means into the couple/uncouple position discussed above. This switch is typically provided on the frame of the invention and when switched, bypasses the other switches so that the drive means cannot be moved by inadvertent operation while coupling or uncoupling the forceps. When switch A is opened, an "idle position" voltage is supplied to comparator 742a by resistor R2 to put the forceps jaws in a closed position with very little force acting on the jaws.

Closing switch B couples the comparator to a different voltage determined by resistor R3 which causes the drive means to exert a greater closing force on the jaws. The force is adjustable by adjusting variable resistor R3, and R3 may be calibrated with indicia to provide the user with specific selections as to the amount of force to be applied to the jaws when the close switch B is closed.

Closing switch C couples the comparator to a negative voltage as determined at resistor R4 to move the jaws to an open position.

It will be appreciated that switches B and C could be embodied as a single pole double throw switch and that these switches could be mounted on an endoscope, in a foot switch, or made responsive to some other type of input.

Figure 18B:
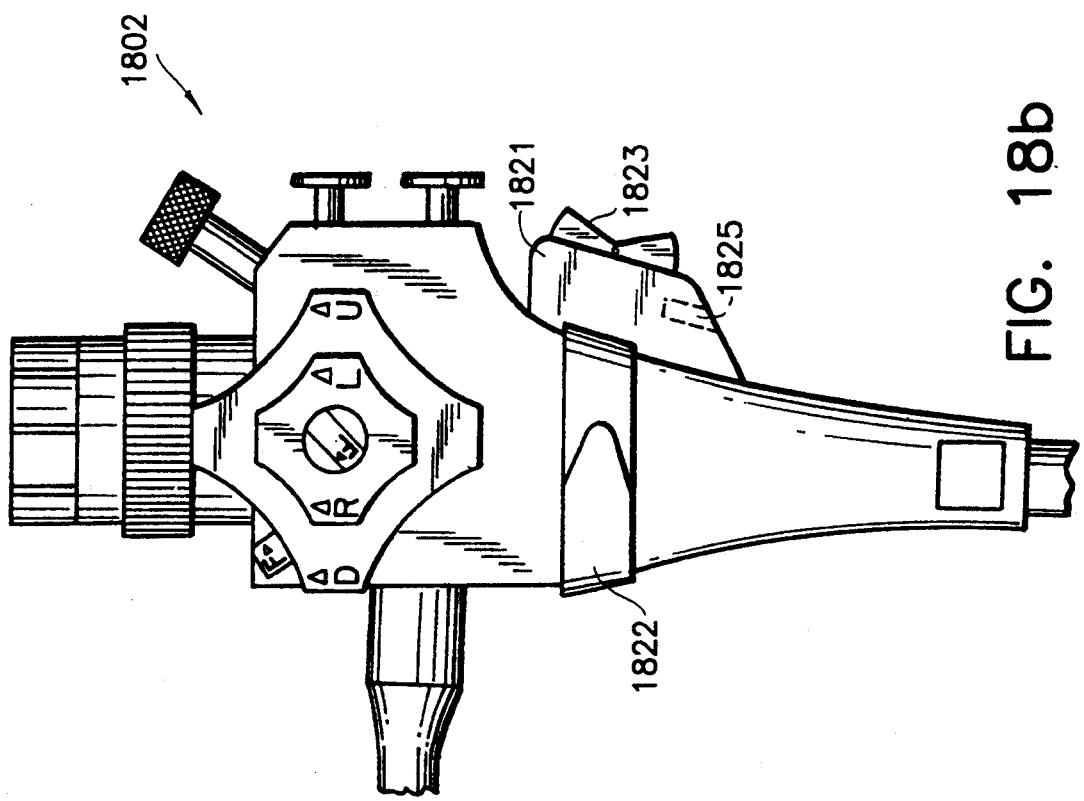
FIG. 18b is a similar view to that of FIG. 18a but with a rocker switch interface.
Figure 18A:
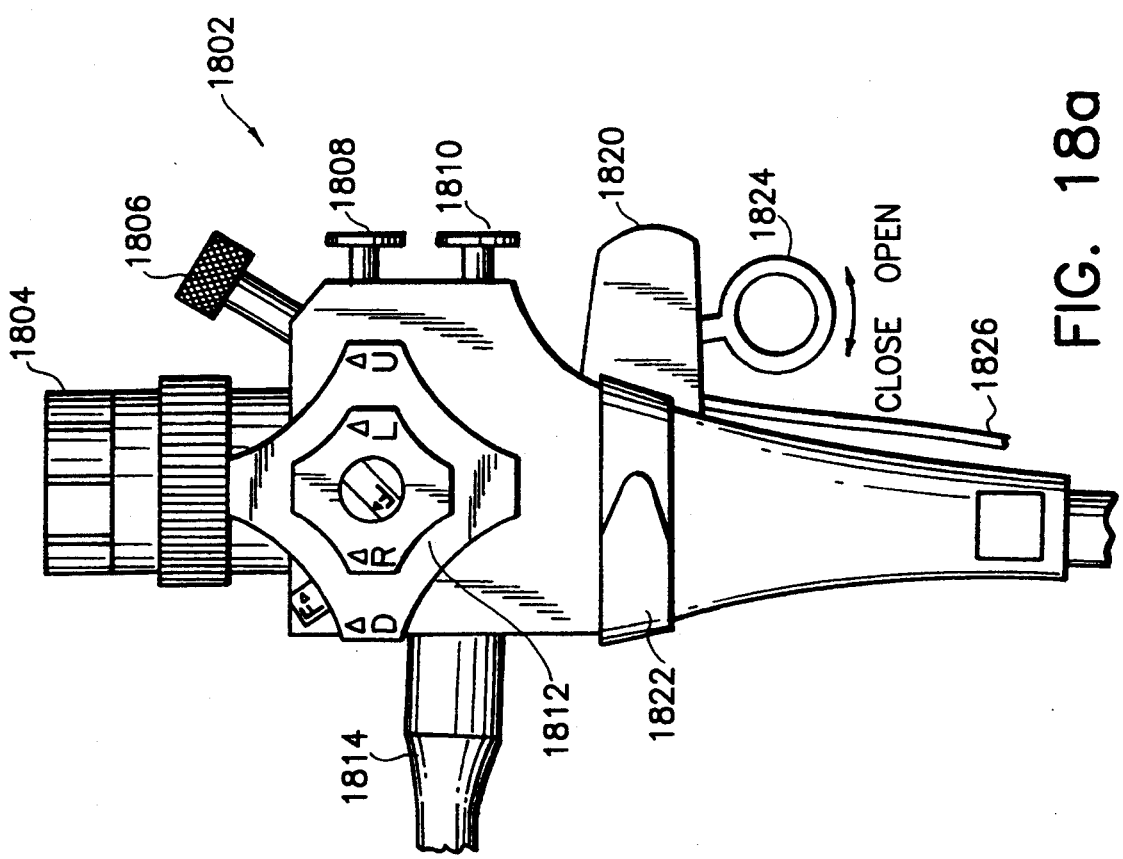
FIG. 18a is a top view of the proximal end of an endoscope with a trigger control interface attached.

FIG. 18a shows one embodiment of the switches described above. Referring now to FIG. 18a, the proximal end 1802 of an endoscope is shown. The endoscope is typically provided with an eye piece 1804, a port 1806 for receiving an endoscopic tool, controls 1808, 1810 for suction/irrigation, controls 1812 for directing the position of the endoscope, and a cable 1814 for electrical, suction and irrigation supply. It will be appreciated, as mentioned above, that both of the surgeon's hands are occupied in holding and manipulating the endoscope and endoscopic tools (e.g., biopsy forceps coil).

In FIG. 18a, the switches described above are embodied in a small switch 1820 which is coupled by a VELCRO strap 1822 or the like to the body of the endoscope 1802 (although the endoscope 1802 could be made with the switch integral therewith). In this particular embodiment, switch 1820 actually includes switches B and C as well as potentiometers R3 and R4 of FIG. 18 which are responsive to a finger operated trigger 1824. The trigger is advantageously spring biased to a central null position. It will thus be appreciated that movement of the trigger in either direction as shown by the arrows in FIG. 18a, results in an opening or closing of the end effectors (switches C and B respectively) with a force proportional to the trigger movement (due to resistors R3 and R4). In this embodiment, switch 1820 is coupled to the controller by a cable 1826. It will be seen from the following description, however, that the coupling of switch 1820 with the controller could also be a wireless coupling.

FIG. 18b shows the same endoscope 1802 with a different switch 1821 similarly attached by VELCRO strap 1822. In this embodiment, switch 1821 incorporates only switches B and C of FIG. 18 which are activated alternatively by rocker mechanism 1823. As shown in FIG. 18b, switch 1821 includes a miniature RF transmitter 1825 for coupling the switch with an RF receiver in the controller (not shown).

Figure 18C:
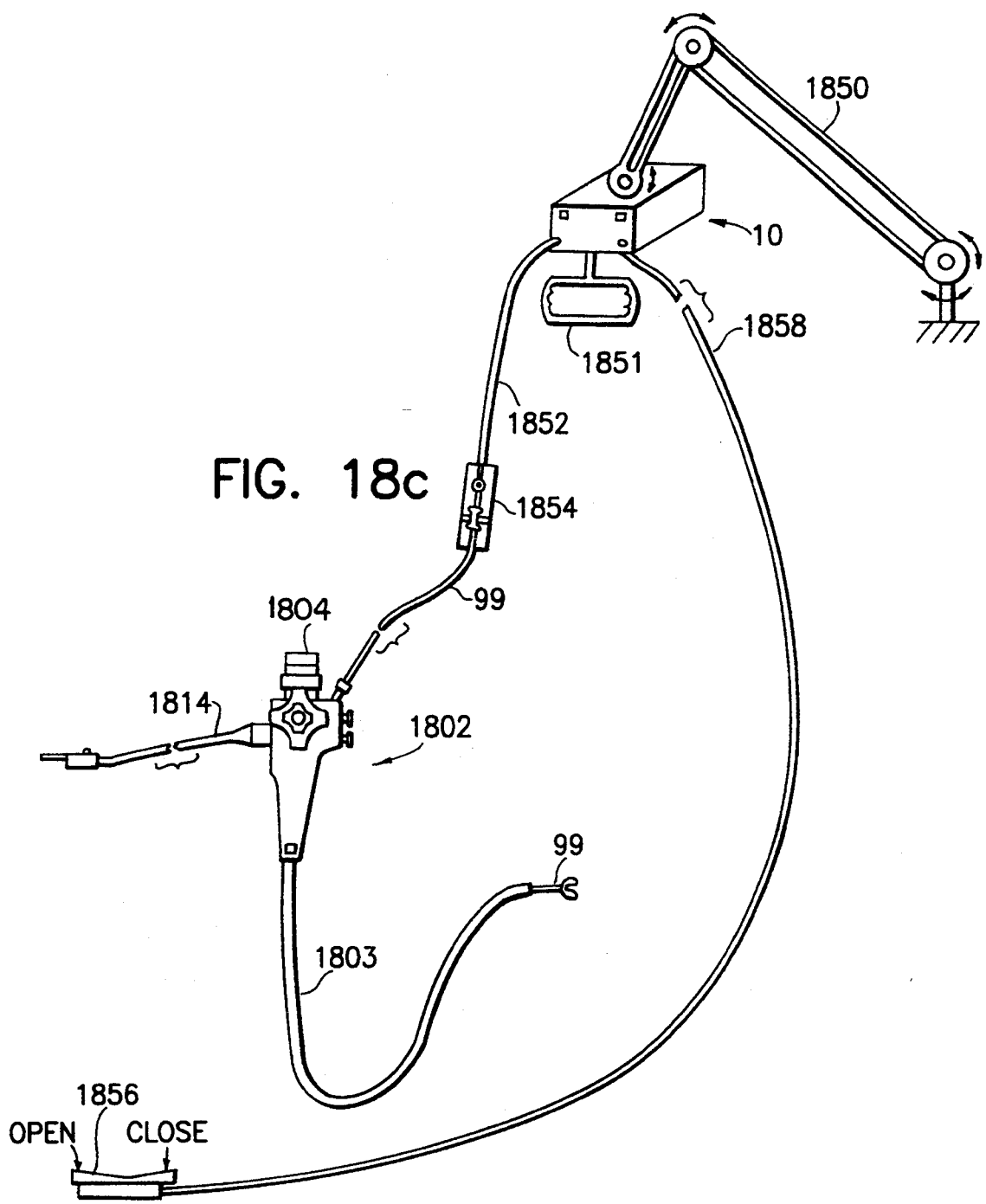
FIG. 18c is a perspective view of the apparatus of the invention in conjunction with an endoscope and endoscopic instrument with a foot switch interface.

FIG. 18c shows an embodiment of the actuator 10 mounted on an articulating arm 1850 for easy positioning relative to a patient (not shown) by grasping handle 1851. This embodiment of the actuator has a coupling device 1854 for receiving a standard biopsy forceps 99. Moreover, as shown in FIG. 18c, the coupling device 1854 is extended from the actuator housing by a coil/pull wire extension 1852.

As shown in FIG. 18c, the biopsy forceps 99 is inserted into a lumen of endoscope 1802 (typically already located in the patient) until the distal end of the forceps 99 extends through the flexible conduit 1803 of the endoscope. The surgeon guides the forceps to the biopsy site while viewing the biopsy site through the eyepiece 1804. The forceps jaws are opened and closed by a footswitch 1856 which is coupled to the actuator 10 by a cable 1858 or by wireless means as described above.

Figure 18D:
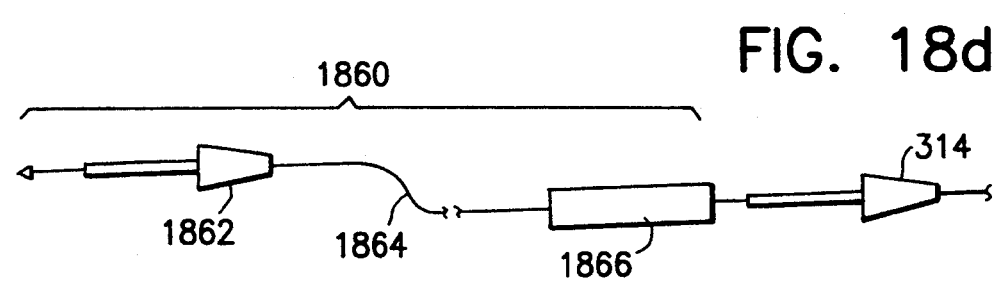
FIG. 18d is a side elevation view of a coil/pull wire extension.

Turning to FIG. 18d, a coil/pull wire extension 1860 is shown. The extension 1860 designed to accept biopsy forceps having a proximal coupling 314 as described in greater detail above with reference to FIGS. 5, 5a, 6 and 6a. As such, it includes a receiving coupling end 1866 for receiving the proximal coupling 314 of forceps 99. The receiving coupling end 1866 is coupled by a coil and pull wire 1864 to an extended proximal coupling 1862 which is insertable in the coupling device 320 of the actuator 300.

Figure 18E:
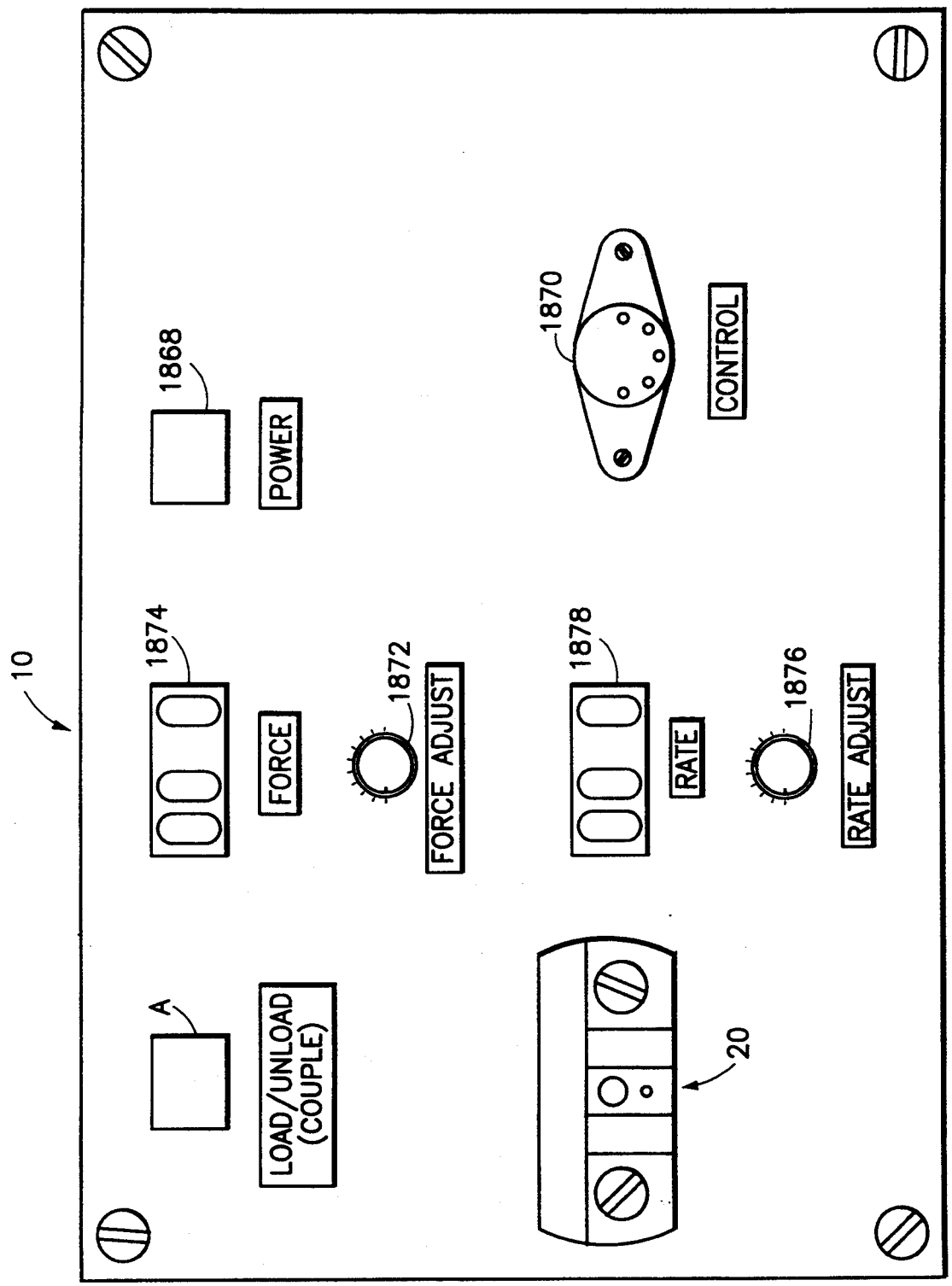
FIG. 18e is a front view of a control face plate for the apparatus of the invention.

FIG. 18e shows the presently preferred embodiment of faceplate controls for the actuator 10. A power ON switch 1868 is provided with an integrated illumination lamp indicating that power is being supplied to the actuator. A similar switch A (described above with reference to FIG. 18) is provided with an integrated illuminated indicator to put the actuator into the forceps coupling position as described above. The forceps coupling device 20 extends out from the face plate. A control coupling jack 1870 is provided for coupling the user interface with the controller. The jack shown is a DIN-5 type, but other types of connections could be used and in the case of wireless or voice activated interface, no jack may be necessary.

According to a preferred embodiment of the invention the force applied by the actuator on the jaws of the forceps is adjustable by potentiometer 1872 and indicated by LED or LCD display 1874. Similarly, the rate of opening and closing of the jaws may be adjusted by potentiometer 1876 which regulates the voltage supply to the excitation legs of amplifier 742a (seen in FIG. 13f) and indicated by LED or LCD 1878. Those skilled in the art will appreciate, however, that many different configurations of the face plate controls are possible.

7B. Voice Control

Figure 19:
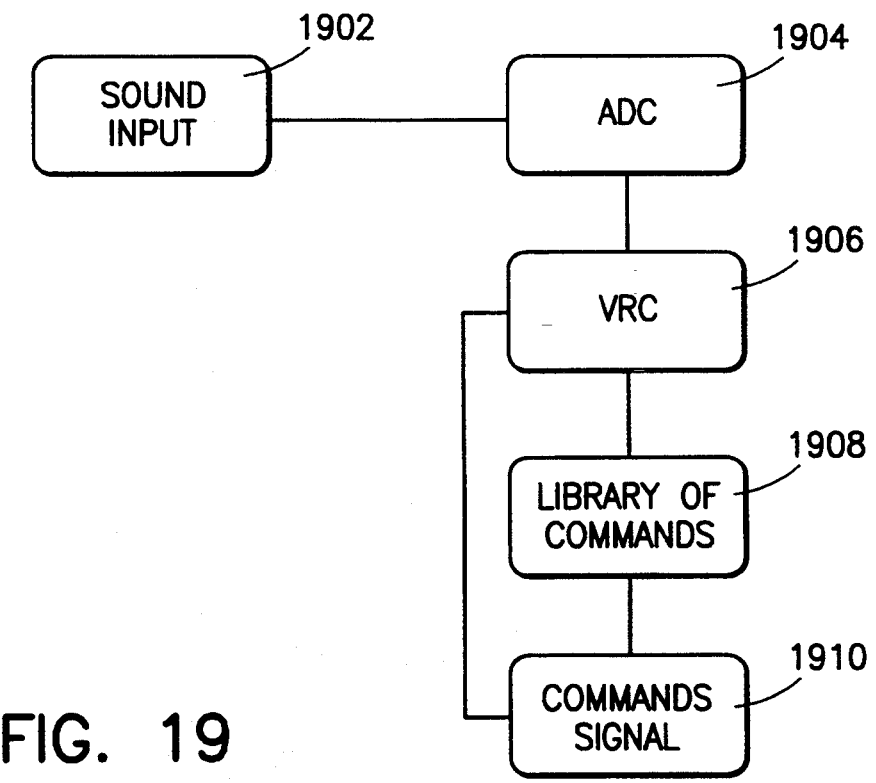
FIG. 19 is a block diagram of a voice activated user interface.

FIG. 19 shows a block diagram of a voice input for controlling the invention. In such an embodiment, as few as two or three voice commands are sufficient to operate forceps. For example: "open", "close", and optionally "idle". Since so few commands are necessary, it is well within the scope of presently available voice recognition technology to provide a voice interface which requires little or no training.

By way of example, a voice interface includes a sound input 1902 coupled to an analog to digital converter 1904 which supplies a digital signal to voice recognition comparator 1906. VRC 1906 compares the signal from the sound input to a library of signals 1908 containing signals representing the voice commands available and generates an appropriate output at 1910 to effect the command recognized. As will be appreciated, the output could be a simple voltage as required by the switch interface described above.

8. Description of the Presently Preferred Embodiment

The presently preferred embodiment of the invention is substantially that as shown in FIGS. 5, 5a, 6, and 6a. A linear actuator is the preferred power source/drive means and a load cell is the preferred sensing/feedback means. The preferred coupling device is either that shown in FIGS. 3 and 4 or FIGS. 5, 5a, 6, and 6a depending on the type of forceps to be used with the invention. The presently preferred controller and user interface are those shown in FIGS. 13f and 18.

The invention is preferably mounted on an articulated arm movable relative to the patient and one or more pullwire/coil extensions are provided.

9. Description of a Simplified Mechanical Embodiment of the Invention

Figure 20A:
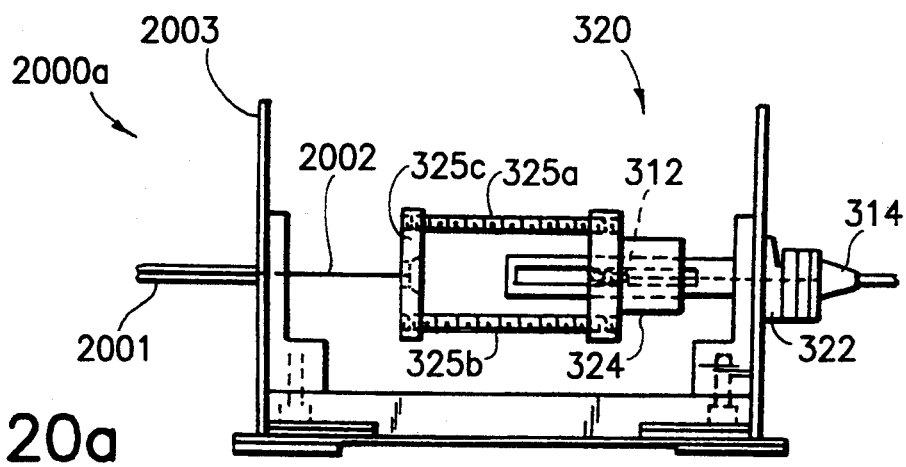
FIG. 20a is a side elevation view of the distal portion of a purely mechanical embodiment of the remote control apparatus of the invention having coupling means for coupling to the distal end of separable biopsy forceps.
Figure 20B:
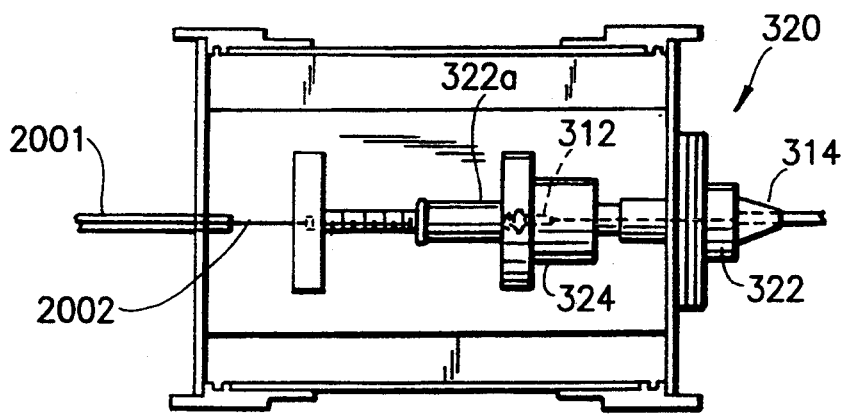
Figure 20C:
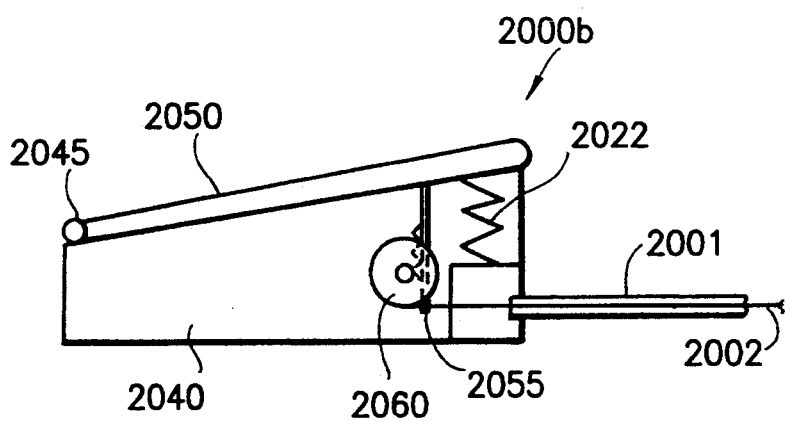

Turning now to FIGS. 20a–20c, in order to further illustrate the concepts of the invention, a purely mechanical embodiment of the remote control actuator is shown. This mechanical embodiment includes a distal portion 2000a having a housing 2003 containing a coupling device 320 for coupling to the activating end 312, 314 of an endoscopic instrument and a proximal controller portion 2000b for remotely actuating the endoscopic instrument. As shown, the distal portion 2000a comprises a coupling device 320 substantially the same as the coupling device described above with reference to FIGS. 5, 5a, 6, and 6a. Unlike the above embodiments, however, the movable part 324 of the coupling device is coupled by rods 325a, 325b and beam 325c to the distal end of a pull wire 2002 contained in a coil 2001. The distal end of coil 2001 is fixedly coupled to the housing 2003. It is anticipated that the coil 2001 and pull wire 2002 extend several meters from the housing 2003 to connect with the proximal remote controller portion 2000b. The exact length of the coil and pull wire will depend on the particular application.

The remote controller portion 2000b includes a foot pedal housing 2040 to which a foot pedal 2050 is hingedly attached at 2045. The foot pedal 2050 is biased upward by a spring 2022. The proximal end of coil 2001 is fixedly coupled to housing 2040 and the proximal end of pull wire 2002 is attached to a pulley 2060 located withing housing 2040. A toothed member extends down from pedal 2050 and engages pulley 2060 such that pressing the pedal down against spring 2022 rotates the pulley 2060 and pulls the pull wire 2002 through the coil 2001. Those skilled in the art will appreciate therefore that stepping on the foot pedal effects a closure of the biopsy jaws and the removing one's foot from the pedal allows action of spring 2022 to open the biopsy jaws. Effectively, then, the surgeon's foot is a power source and/or a control means; the pulley/gear mechanism 2060 inside the foot pedal is the drive means; the top of the pedal 2050 is the interface means; and the coupling means is the coupling device 320.

There have been described and illustrated herein several embodiments of a remote control actuator for an endoscopic instrument. While particular embodiments of the invention have been described, it is not intended that the invention be limited thereto, as it is intended that the invention be as broad in scope as the art will allow and that the specification be read likewise. Thus, while particular coupling devices have been disclosed, it will be appreciated that other coupling devices could be utilized. Also, while a number of different power sources and drive means have been shown, it will be recognized that other power sources and drive means could be used with similar results obtained. Moreover, while particular configurations have been disclosed in reference to the actuation of biopsy forceps, it will be appreciated that other configurations could be used to actuate other endoscopic instruments, including laparoscopic instruments as well. Furthermore, while the user interface has been disclosed as having input for a limited number of operations such as open, close, and idle, it will be understood that different and/or other operations can be provided as required by different types of endoscopic instruments, for example, cautery, suction, and irrigation instruments. In addition, it will be appreciated that aspects of particular embodiments of the invention can be utilized in conjunction with aspects of other embodiments. For example, foot switches, hand activated switches, and voice actuation may be combined with each other in different ways as desired. In fact, a plurality of foot switches could be utilized, with e.g., one for open, another for close, and a default of "idle". It will therefore be appreciated by those skilled in the art that yet other modifications could be made to the provided invention without deviating from its spirit and scope as so claimed.

We claim:

1. A remotely operable actuator for use with an endoscopic tool having a hollow tubular member and a control member extending through the tubular member, at least one end effector coupled to the distal ends of the tubular member and the control member, the tubular member and the control member having a proximal actuating end where the control member is movable through the tubular member to actuate the tool and effect movement of the at least one end effector, said actuator comprising:
   a) coupling means adapted for mechanically attaching said actuator to the proximal actuating end of the tool;
   b) drive means coupled to said coupling means for moving said coupling means to effect actuation of the tool;
   c) power source means coupled to said drive means for powering said drive means;
   d) interface means for accepting commands from a user to at least partially control said moving of said drive means, said interface means coupled to one of said drive means and said power source means.

2. An actuator according to claim 1, further comprising:
   e) control means coupling said interface means to one of said drive means and said power source means, said control means for controlling said moving of said drive means.

3. An actuator according to claim 2, further comprising:
   f) sensing/feedback means coupled to said drive means and to said control means for sensing one of a position of said drive means and a force supplied by said drive means to said coupling means.

4. An actuator according to claim 1, wherein:
the proximal actuating end includes a thumb ring and a spool,
said coupling means includes thumb ring coupling means for attaching the thumb ring to said actuator and spool coupling means for attaching the spool to said actuator, and
said moving of said coupling means moves at least one of the spool relative to the thumb ring and the thumb ring relative to the spool.

5. An actuator according to claim 1, wherein:
the proximal actuating end includes first and second actuating members movable relative to each other,
said coupling means includes first and second coupling members for attaching the respective first and second actuating members to said actuator, at least one of said coupling members being movable, and
said moving of said coupling means moves at least one of the first coupling member relative to the second coupling member and the second coupling member relative to the first coupling member.

6. An actuator according to claim 1, wherein:
the proximal actuating end includes a pull wire and a coil surrounding said pull wire,
said coupling means includes a pull wire coupling means for attaching the pull wire to said actuator and a coil coupling means for attaching the coil to said actuator; and
said moving of said coupling means moves at least one of the pull wire relative to the coil and the coil relative to the pull wire.

7. An actuator according to claim 1, wherein:
said drive means comprises a linear actuator.

8. An actuator according to claim 1, wherein:
said drive means comprises an electric motor.

9. An actuator according to claim 8, wherein:
said motor is a stepper motor.

10. An actuator according to claim 8, wherein:
said drive means further comprises a belt and a pulley.

11. An actuator according to claim 8, wherein:
said drive means further comprises a motor, a chain and a sprocket.

12. An actuator according to claim 8, wherein:
said drive means further comprises a rack and a pinion.

13. An actuator according to claim 1, wherein:
said drive means comprises a piston and a cylinder.

14. An actuator according to claim 7, wherein:
said power source means comprises an electrical power supply.

15. An actuator according to claim 8, wherein:
said power source means comprises an electrical power supply.

16. An actuator according to claim 13, wherein:
said power source means comprises compressed air.

17. An actuator according to claim 13, wherein:
said power source means comprises pressurized hydraulic fluid.

18. An actuator according to claim 14, further comprising:
   e) control means coupling said interface means to one of said drive means and said power source means, said control means for controlling said moving of said drive means, wherein said control means comprises an electronic control circuit.

19. An actuator according to claim 15, further comprising:
   e) control means coupling said interface means to one of said drive means and said power source means, said control means for controlling said moving of said drive means, wherein said control means comprises an electronic control circuit.

20. An actuator according to claim 16, further comprising:

e) control means coupling said interface means to one of said drive means and said power source means, said control means for controlling said moving of said drive means, wherein said control means comprises a fluid metering valve.

21. An actuator according to claim 17, further comprising:
e) control means coupling said interface means to one of said drive means and said power source means, said control means for controlling said moving of said drive means, wherein said control means comprises a fluid metering valve.

22. An actuator according to claim 1, wherein:
said interface means comprises a foot switch coupled to said control means by a wire.

23. An actuator according to claim 1, wherein:
said interface means comprises a voice recognition circuit.

24. An actuator according to claim 1, wherein:
said interface means comprises a foot switch coupled to said control means by a wireless coupling.

25. An actuator according to claim 1, wherein:
said interface means comprises a finger actuated trigger switch coupled to an endoscope.

26. An actuator according to claim 1, wherein:
said interface means comprises a finger actuated rocker switch coupled to an endoscope.

27. An actuator according to claim 2, wherein:
said control means includes a comparator circuit having an input coupled to said interface means and an output coupled to said drive means.

28. An actuator according to claim 2, wherein:
said control means includes a flow metering valve coupled to said power source and said drive means.

29. An actuator according to claim 3, wherein:
said sensing/feedback means comprises a load cell coupled to said control means.

30. An actuator according to claim 3, wherein:
said sensing/feedback means comprises a position sensor coupled to said control means.

31. An actuator according to claim 30, wherein:
said position sensor is further provided with a spring which biases said position sensor to an extreme position.

32. An actuator according to claim 31, wherein:
said position sensor comprises a linear variable displacement transducer.

33. An actuator according to claim 31, wherein:
said position sensor comprises a variable resistor.

34. An actuator according to claim 31, wherein:
said position sensor comprises a proximity switch.

35. An actuator according to claim 3, wherein:
said sensing/feedback means comprises a current sensor and a comparator.

36. An actuator according to claim 3, wherein:
said sensing/feedback means comprises a fluid pressure sensor.

37. An actuator according to claim 3, wherein:
said control means comprises means for maintaining a constant force on the actuating end of the endoscopic tool in the absence of said user commands.

38. An actuator according to claim 37, where the endoscopic tool includes a pair of end effectors which are responsive to a force applied on the actuating end of the endoscopic tool, wherein:
said constant force holds the end effectors in a closed position.

39. An actuator for remote actuation of an endoscopic tool having a hollow tubular member and a control member extending through the tubular member, at least one end effector coupled to the distal ends of the tubular member and the control member, the tubular member and the control member having a proximal actuating end where the control member is movable through the tubular member to actuate the tool and effect movement of the at least one end effector, said actuator comprising:
a) a flexible coil having an internal pull wire;
b) a coupling device coupled to a distal end of said coil and a distal end of said pull wire, said coupling device being adapted to couple the proximal actuating end of the endoscopic tool to said distal end of said coil and said distal end of said pull wire; and
c) drive means coupled to a proximal end of said coil and pull wire for moving one of said coil and pull wire relative to another.

40. An actuator according to claim 39, wherein:
said drive means comprises a mechanical foot switch coupled to said proximal end of said coil and pull wire such that stepping on said foot switch moves one of said coil and pull wire relative to another.

41. An actuator according to claim 40, wherein:
said foot switch comprises a pulley coupled to said pull wire, a foot pedal coupled to said pulley, and a spring means biasing said foot pedal to a first position, whereby pressing said foot pedal against said spring means rotates said pulley to pull said pull wire.

42. An extension device for use with an endoscopic tool having a hollow tubular member and a control member extending through the tubular member, at least one end effector coupled to the distal ends of the tubular member and the control member, the tubular member and the control member having a proximal actuating end where the control member is movable through the tubular member to actuate the tool and effect movement of the at least one end effector, said extension device for coupling the proximal actuating end to a remotely located actuator, said extension device comprising:
a) a flexible coil having an internal pull wire;
b) a first coupling device coupled to a distal end of said coil and a distal end of said pull wire, said first coupling device being adapted to couple the proximal actuating end of the endoscopic tool to said distal end of said coil and said distal end of said pull wire; and
c) a second coupling device coupled to a proximal end of said coil and a proximal end of said pull wire, said second coupling device being adapted to couple said proximal end of said coil and said proximal end of said pull wire to said remotely located actuator.

43. An extension device according to claim 42, wherein:
the actuating end of the endoscopic tool includes a thumb ring and a spool and said first coupling means comprises a spool cradle and a thumb ring engaging boss, said boss being coupled to said pull wire.

44. An extension device according to claim 42, wherein:
said first coupling device and said second coupling device are matable male and female devices.

* * * * *